(12) United States Patent
Nishikado et al.

(10) Patent No.: US 10,276,012 B2
(45) Date of Patent: Apr. 30, 2019

(54) DISPLAY DEVICE AND DISPLAY METHOD FOR SYSTEM FOR MONITORING PERSON TO BE MONITORED, AND SYSTEM FOR MONITORING PERSON TO BE MONITORED

(71) Applicant: KONICA MINOLTA, INC., Chiyoda-ku, Tokyo (JP)

(72) Inventors: Masashi Nishikado, Osaka (JP); Atsuhiro Noda, Ashiya (JP); Aki Tsuji, Kyoto (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/751,286

(22) PCT Filed: Jul. 27, 2016

(86) PCT No.: PCT/JP2016/072000
§ 371 (c)(1),
(2) Date: Feb. 8, 2018

(87) PCT Pub. No.: WO2017/026283
PCT Pub. Date: Feb. 16, 2017

(65) Prior Publication Data
US 2018/0233013 A1     Aug. 16, 2018

(30) Foreign Application Priority Data

Aug. 10, 2015   (JP) .................................. 2015-158154

(51) Int. Cl.
*G08B 5/22*         (2006.01)
*G08B 21/02*        (2006.01)
(Continued)

(52) U.S. Cl.
CPC ............. *G08B 21/02* (2013.01); *A61G 12/00* (2013.01); *G06F 3/04842* (2013.01);
(Continued)

(58) Field of Classification Search
CPC ... A61B 5/14532; A61B 5/742; A61B 5/0022; A61B 5/6898; A61B 5/7475;
(Continued)

(56) References Cited

U.S. PATENT DOCUMENTS

2006/0264785 A1* 11/2006 Dring .................... A61B 5/1115
                                                                    600/595
2012/0229634 A1*  9/2012 Laett .................... G08B 21/043
                                                                    348/143
(Continued)

FOREIGN PATENT DOCUMENTS

JP       S6326798 A     2/1988
JP    2004334763 A     11/2004
(Continued)

OTHER PUBLICATIONS

International Search Report corresponding to Application No. PCT/JP2016/072000; dated Oct. 11, 2016.
(Continued)

*Primary Examiner* — Daniel Previl
(74) *Attorney, Agent, or Firm* — Cantor Colburn LLP

(57) ABSTRACT

In a display device, a display method, and a subject observation system according to the present invention, when a sensor unit inspects a predetermined movement of a subject to be observed, a display device receives a new inspection result about the inspection from the sensor unit via a central processing apparatus. In this case, the display part displays a code representing a presence of the new inspection result having been received, while maintaining an existing display content being displayed thereon, and further displays the
(Continued)

new inspection result having been received on the display part when an input part receives a change instruction input.

9 Claims, 13 Drawing Sheets

(51) Int. Cl.
| | | |
|---|---|---|
| *A61G 12/00* | (2006.01) | |
| *G08B 25/04* | (2006.01) | |
| *H04N 7/18* | (2006.01) | |
| *G16H 40/67* | (2018.01) | |
| *G08B 25/01* | (2006.01) | |
| *G08B 25/08* | (2006.01) | |
| *G08B 21/04* | (2006.01) | |
| *G06F 3/0484* | (2013.01) | |

(52) U.S. Cl.
CPC ..... *G08B 21/0407* (2013.01); *G08B 21/0461* (2013.01); *G08B 21/0476* (2013.01); *G08B 25/014* (2013.01); *G08B 25/04* (2013.01); *G08B 25/08* (2013.01); *G16H 40/67* (2018.01); *H04N 7/18* (2013.01)

(58) Field of Classification Search
CPC . A61B 5/486; A61B 5/681; A61B 2562/0295; A61B 5/0004; A61B 5/02125; A61B 5/6801; A61B 5/6803; A61B 2560/045; A61B 3/0025

USPC ........ 340/286.07, 573.1, 531, 539.1, 539.16, 340/665, 541, 573.4, 573.5, 286.11, 340/286.01
See application file for complete search history.

(56) References Cited

U.S. PATENT DOCUMENTS

| | | | |
|---|---|---|---|
| 2013/0018255 A1* | 1/2013 | Kitamura | A61B 1/00009 600/424 |
| 2013/0267873 A1 | 10/2013 | Fuchs | |
| 2014/0267663 A1 | 9/2014 | Yasukawa et al. | |
| 2014/0322815 A1* | 10/2014 | Carlsgaard | G01N 33/66 436/95 |
| 2014/0344714 A1 | 11/2014 | Toyoshima et al. | |
| 2018/0020931 A1* | 1/2018 | Shusterman | A61B 5/02055 600/483 |

FOREIGN PATENT DOCUMENTS

| | | | |
|---|---|---|---|
| JP | 2013120569 A | | 6/2013 |
| JP | 2014090913 A | | 5/2014 |
| JP | 2015058030 | * | 3/2015 |
| JP | 2015058030 A | | 3/2015 |

OTHER PUBLICATIONS

Extended European Search Report corresponding to Application No. 16834980.1-1206/3330937 PCT/JP2016072000; dated Jul. 23, 2018.

* cited by examiner

FIG.4

| 51-SV (51-TA) | 52-SV (52-TA) | 53-SV (53-TA) | 54-SV (54-TA) | 55-SV (55-TA) | 56-SV (56-TA) |
|---|---|---|---|---|---|
| SENSOR ID | EVENT TYPE | EVENT TIME (RECEIPT TIME) | STILL IMAGE (FILE NAME) | VIDEO IMAGE (IP ADDRESS) | ACTION |
| SU-1 | WAKING-UP MOVEMENT | 06:32 | SP1 | .*.. | 0 |
| SU-1 | LEAVING MOVEMENT FROM BED | 06:45 | SP2 | .*.. | 0 |
| SU-2 | WAKING-UP MOVEMENT | 06:48 | SP3 | .*.. | 0 |
| SU-2 | FALLING DOWN | 06:50 | SP4 | .*.. | 1 |
| ... | ... | ... | ... | ... | ... |
| ... | ... | ... | ... | ... | ... |

↙ MT-SV (MT-TA)

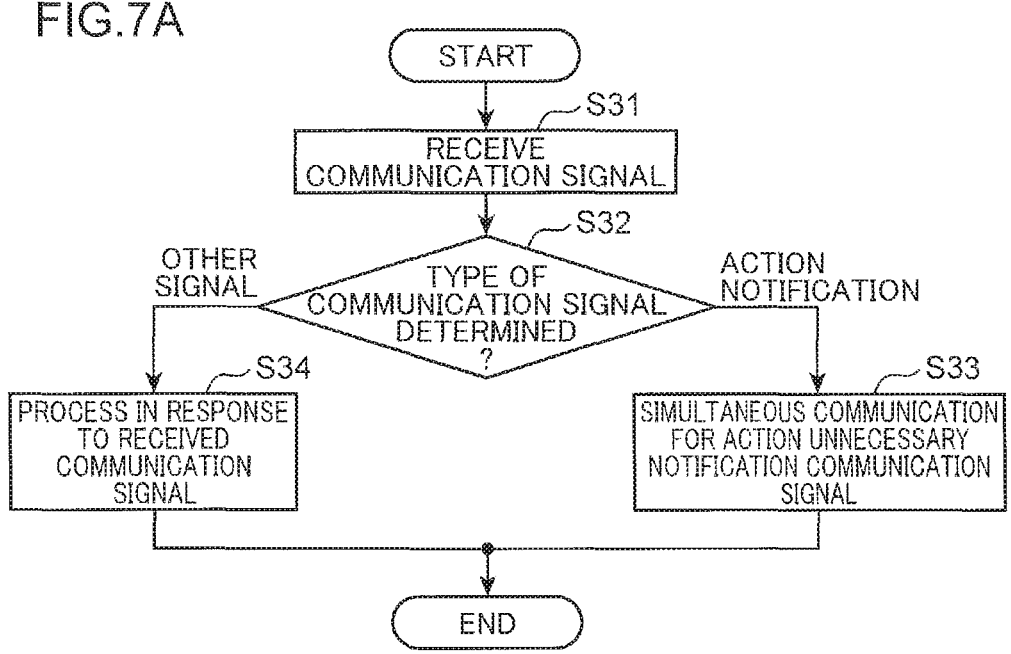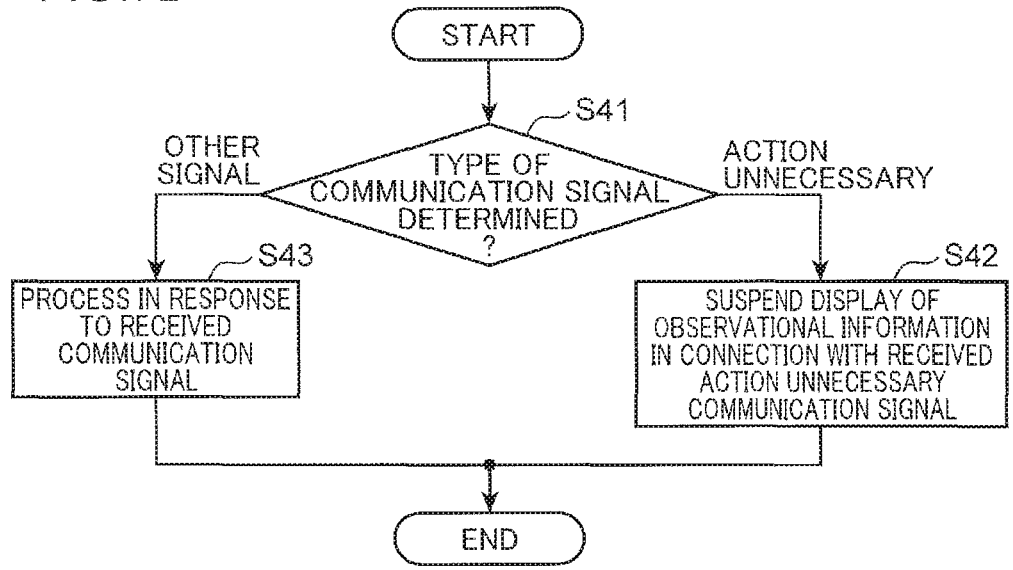

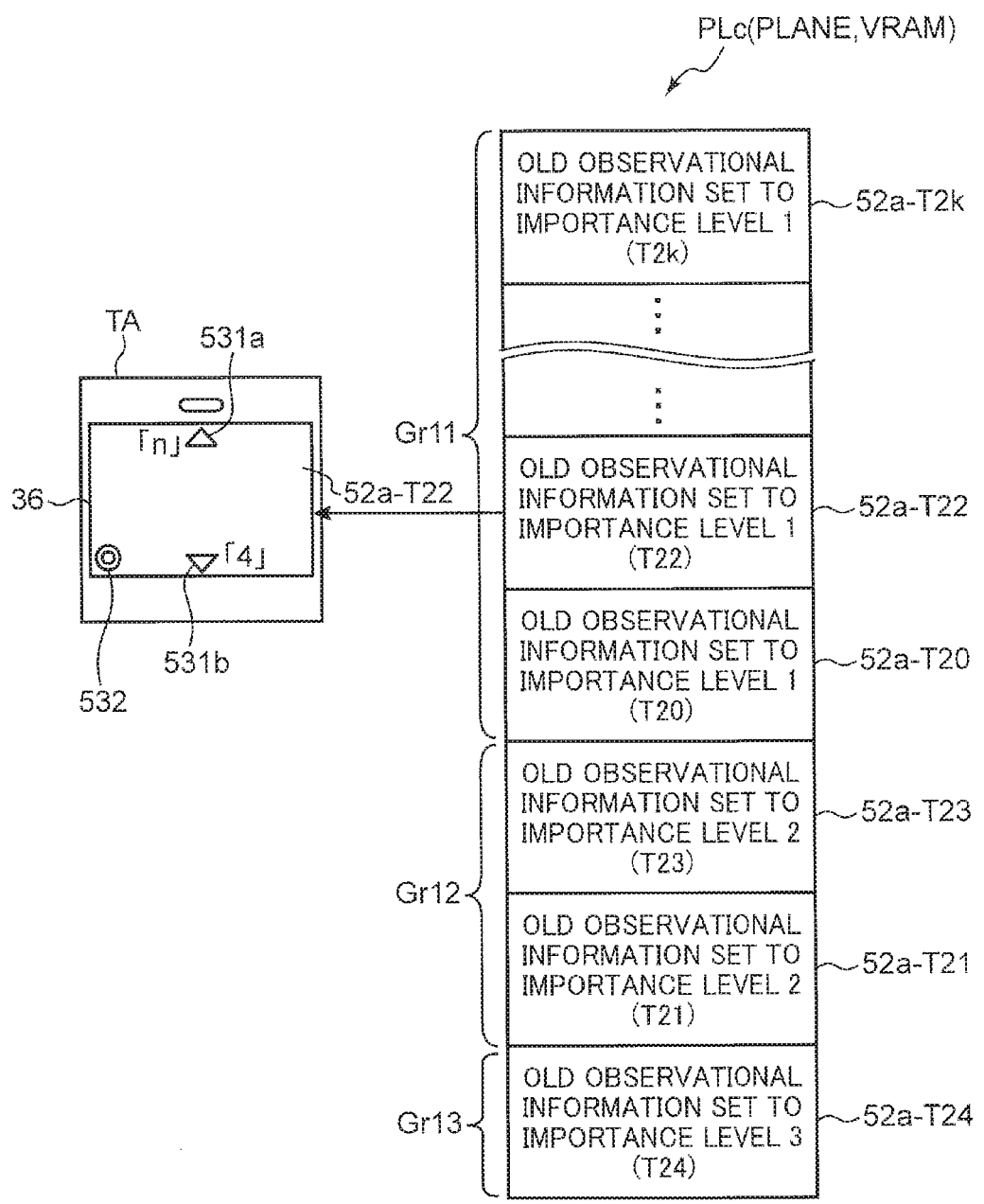

DISPLAY DEVICE AND DISPLAY METHOD FOR SYSTEM FOR MONITORING PERSON TO BE MONITORED, AND SYSTEM FOR MONITORING PERSON TO BE MONITORED

CROSS REFERENCE TO RELATED APPLICATIONS

This is the U.S. national stage of application No. PCT/JP2016/072000, filed on Jul. 27, 2016. Priority under 35 U.S.C. § 119(a) and 35 U.S.C. § 365(b) is claimed from Japanese Application No. 2015-158154, filed Aug. 10, 2015, the disclosure of which is incorporated herein by reference.

TECHNICAL FIELD

The present invention relates to a display device and a display method for use in a subject observation system for observing a subject as a watching target in cooperation with a plurality of devices, and a subject observation system.

BACKGROUND

Our country, Japan, has been experiencing an aging society, particularly, a super aging society where an aging rate of the population aged 65 and older to the total population exceeds 21% because of improvements in living standards, sanitary conditions and medical levels accompanying with the rapid economic growth after the war. Also, the population aged 65 and older is expected to reach approximately 34,560,000 to the total population of 124,110,000 in 2020, while the population aged 65 and older was approximately 25,560,000 to the total population of approximately 127,650,000 in 2005. This aging society is expected to have a greater number of nursing or care needers (nursing needers or the like) due to illnesses, injuries or aging than a non-aging society. Moreover, our country also has been experiencing a declining-birth rate society, for example, the total fertility rate was 1.43 in 2013. This circumstance has also caused a problem of "care of an elderly person by another elderly person", which means that an elderly person who requires nursing or the like has to be taken care of by an elderly family member such as a spouse, child, or sibling.

The nursing needers or the like enter hospitals or facilities like welfare facilities (including short-stay facilities, care homes, intensive care homes, and the like referred by Japanese statutory laws) for the elderly, and receive nursing or care. These facilities face risks that nursing needers or the like get injuries by falling down from beds or falling over during walking, or loiter after sneaking out of the beds. In consideration that it is necessary to eliminate the risks as soon as possible and that the risks may lead to more serious problems if being left without any countermeasures, nurses and caregivers or the like confirm the safety or check the state of each of the nursing needers or the like through regular patrols.

However, the nursing and care industries encounter a problem of chronic labor shortage due to a slower increase in the number of nurses or the like than in the number of nursing needers or the like. Furthermore, compared with the day time, a workload per nurse or caregiver is much heavier during the semi-night time and the night time because of a decrease in the number of nurses or caregivers during those times. Hence, there has been a demand of reduction in the workload. Moreover, the aforementioned problem of "care of an elderly person by another elderly person" is seen in the facilities as well without exception, i.e., it is often recognized that an elderly nurse or the like has to take care of an elderly care needer or the like. Generally, as one gets older, his or her physical strength declines. This means that the nursing workload is harder for an older nurse than for a younger nurse regardless of his or her good health, and the older nurse is considered to delay in movement or judgment.

In order to alleviate the labor shortage and the workload of the nurses or the like, technologies of supporting the nursing and caring workloads have been demanded. In response to this demand, subject observation apparatuses have been recently researched and developed to observe (monitor) a subject as a watching target, such as a nursing needer or the like, to be observed.

The technologies involve an exemplary call system disclosed in Patent Literature 1. The call system disclosed in Patent Literature 1 includes a subsidiary nurse call device allotted to a bed for allowing a patient to call a nurse, and a host nurse call device arranged in a nurse station for answering to the calling from the subsidiary nurse call device, and further has a camera for photographing the patient on the bed from a higher position than the bed, and state judging means for judging an occurrence of at least one of the states of the patient, i.e., raising his/her upper body and leaving away from the bed, thereby outputting a caution state occurrence signal. The host nurse call device has notification means for performing a notification upon receipt of the caution state occurrence signal. Also, the nurse call system further includes a mobile terminal carried by the nurse in order to answer to the calling from the subsidiary nurse call device, and communication control means for sending a video image photographed by the camera to the mobile terminal upon receipt of the caution state occurrence signal.

Meanwhile, a person living alone is also a subject to be observed as well as the nursing needer or the like in terms of safety confirmation.

Moreover, in the nurse call system disclosed in Patent Literature 1, a caution state occurrence is notified to the mobile terminal (for example, paragraph [0029] of Patent Literature 1). However, Patent Literature 1 does not disclose any way of displaying a new caution state occurrence on the mobile terminal having received information thereof, and thus it is unclear how the new caution state occurrence is displayed. If the new caution state occurrence overlaps a previously notified caution state occurrence so as to be displayed, there is a risk of delay in an action (execution, reply) to a patient who is in a state in connection with to the previously notified caution state occurrence.

CITATION LIST

Patent Literature

Patent Literature 1: Japanese Unexamined Patent Publication No. 2014-90913

SUMMARY

The present invention has been accomplished in view of the above-described situations. An object of the present invention is to provide a display device and a display method for use in a subject observation system which can ensure an encouragement of an action (execution, reply) to a patient in connection with a previous notification, and a subject observation system.

In a display device, a display method, and a subject observation system according to the present invention, when a sensor unit inspects a predetermined movement of a subject to be observed, a display device receives a new inspection result about the inspection from the sensor unit via a central processing apparatus. In this case, the display part displays a code representing a presence of the new inspection result having been received, while maintaining an existing display content being displayed thereon, and further displays the new inspection result having been received on the display part when an input part receives a change instruction input.

These and other subjects, features and advantages of the present invention will become more apparent upon reading the following detailed description along with the accompanying drawings.

BRIEF DESCRIPTION OF THE DRAWINGS

FIG. 4 shows a configuration of an observational information table stored in both the administration server and the mobile terminal device in the subject observation system.

FIG. 7 is a flowchart showing an operation for deleting an observational information screen image in the subject observation system.

FIG. 13 is a diagram illustrating a third storage way to be executed in the display screen image storage part of the mobile terminal device in the subject observation system.

DESCRIPTION OF EMBODIMENTS

Figure 1:
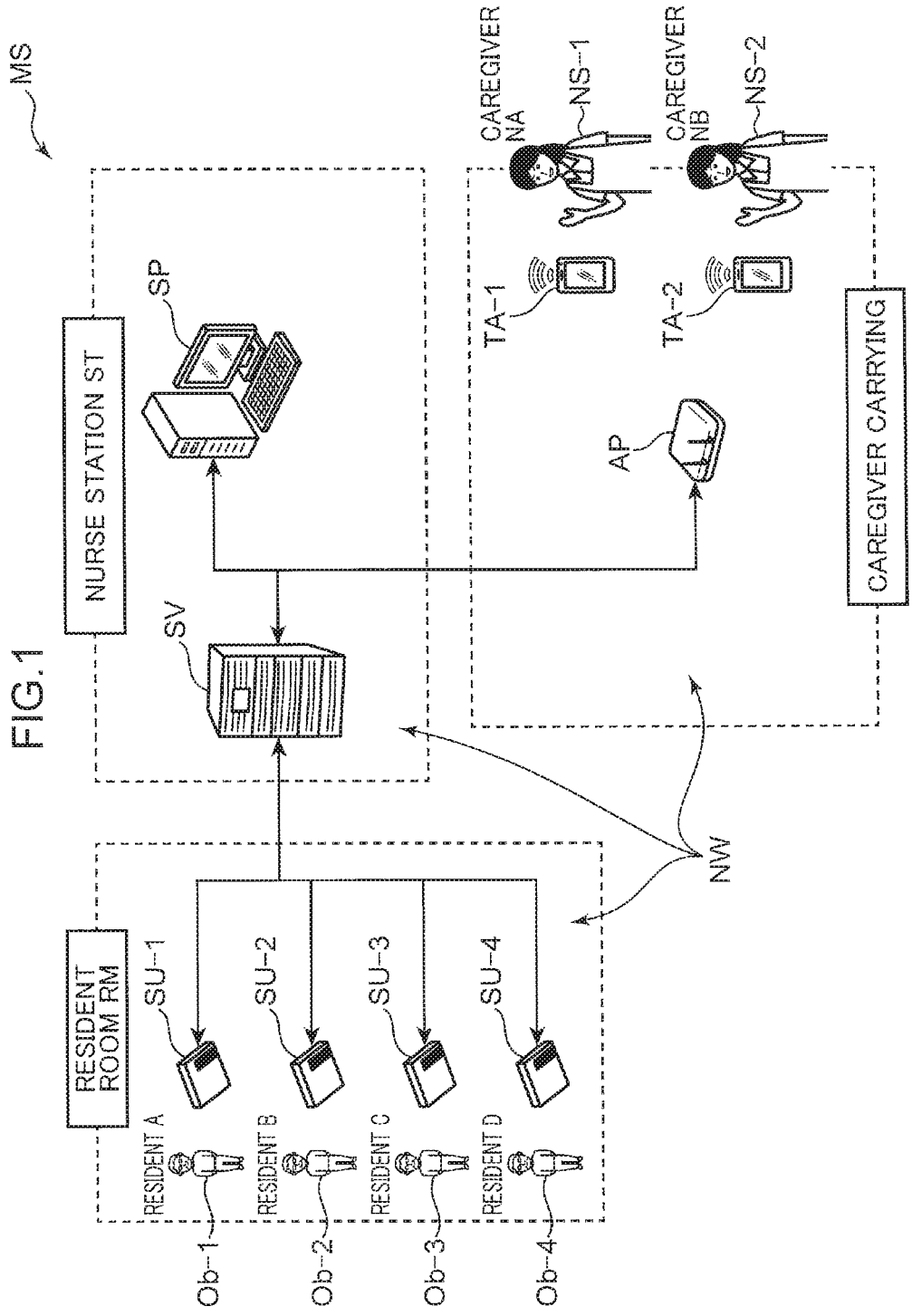
FIG. 1 shows a configuration of a subject observation system according to an embodiment of the present invention.

Hereinafter, an embodiment of the present invention will be described with reference to the accompanying drawings. Elements denoted by the same reference numerals in the drawings have the same configuration and, therefore, repeated descriptions will be appropriately omitted. In the present specification, elements are denoted by a same reference numeral when being referred to collectively, and are denoted by a same reference numeral accompanied by a different respective reference character when being referred to individually.

Figure 2:
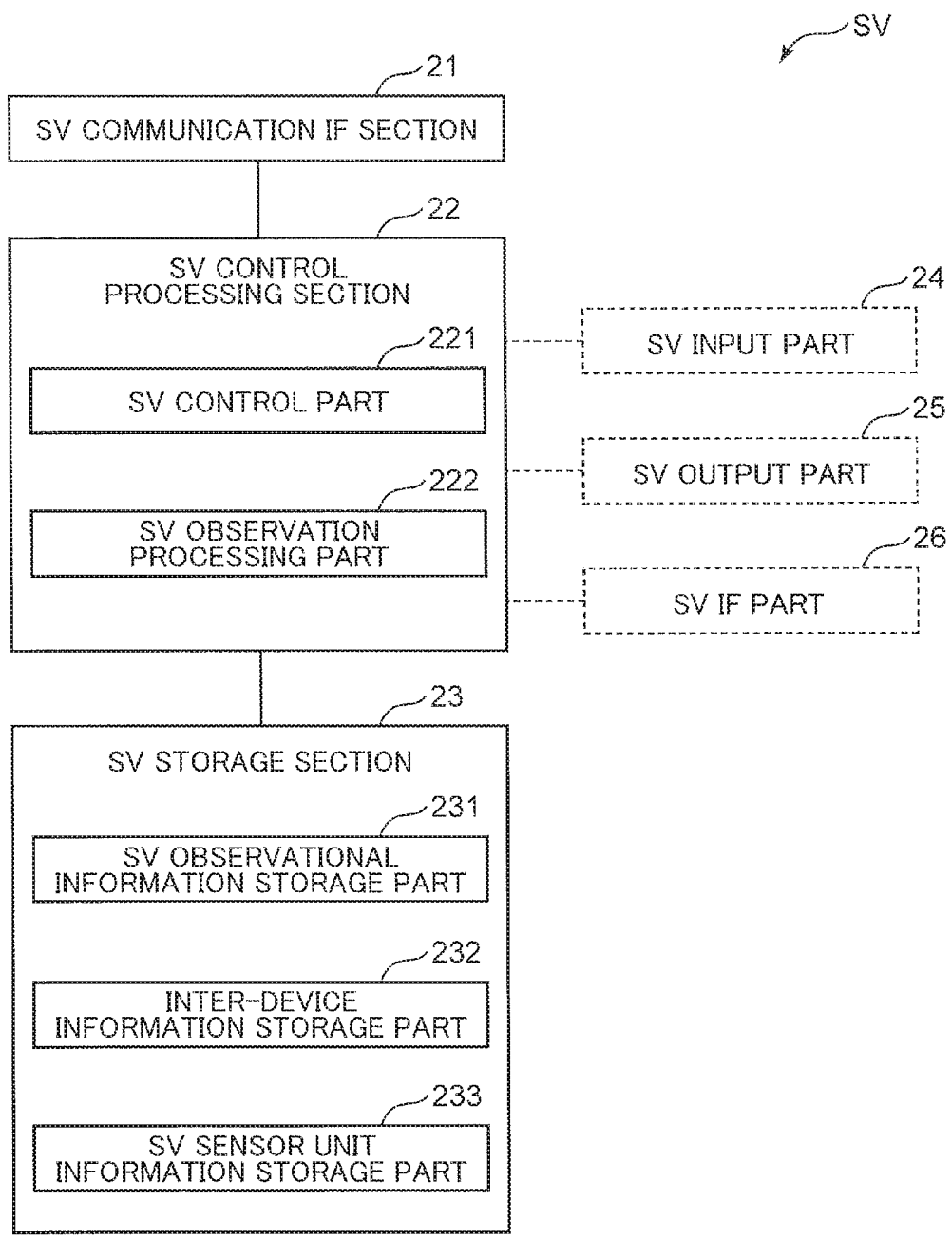
FIG. 2 shows a configuration of an administration server for use in the subject observation system.
Figure 3:
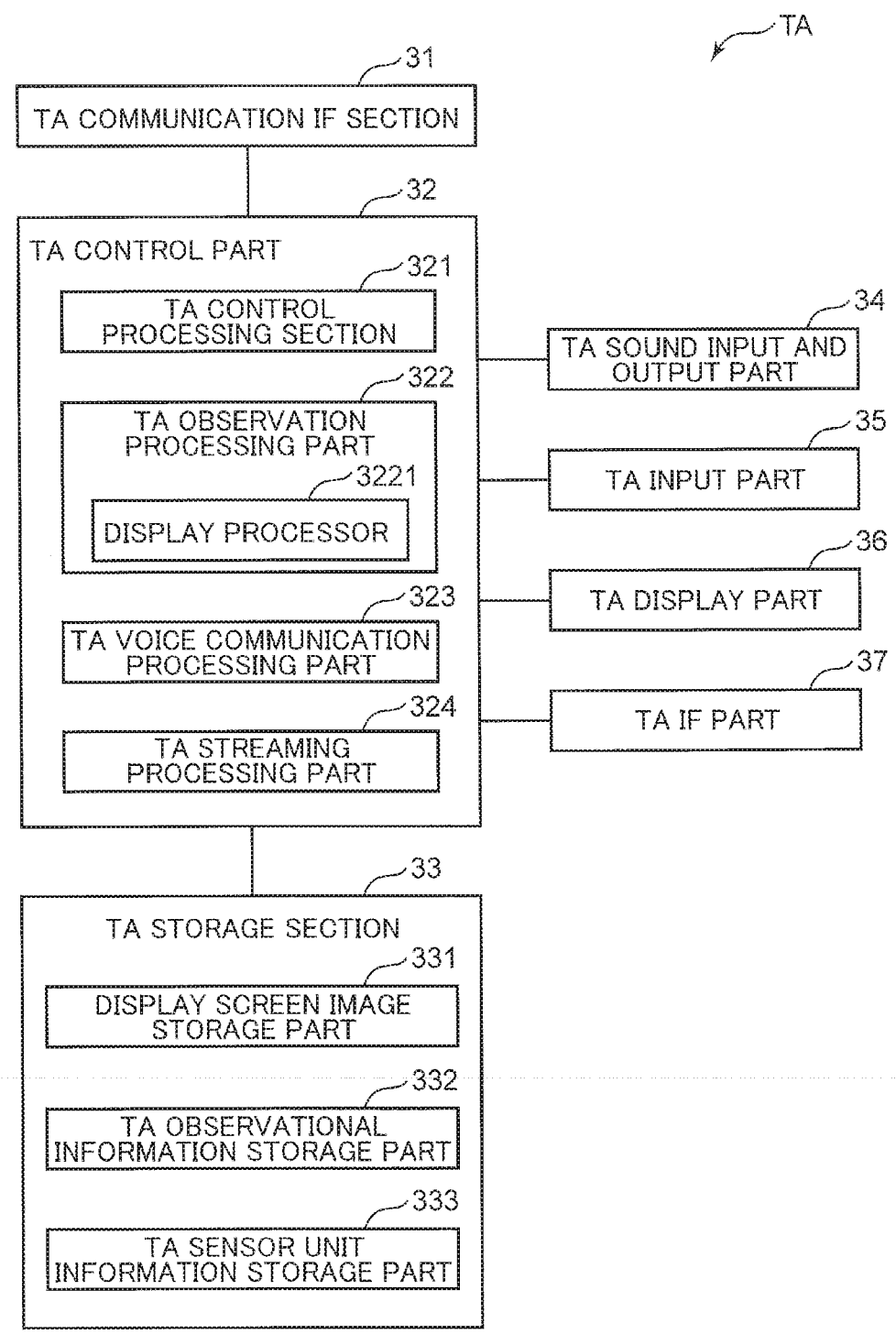
FIG. 3 shows a configuration of a mobile terminal device for use in the subject observation system.

FIG. 1 shows a configuration of a subject observation system of the embodiment. FIG. 2 shows a configuration of an administration server for use in the subject observation system of the embodiment. FIG. 3 shows a configuration of a mobile terminal device for use in the subject observation system of the embodiment. FIG. 4 shows a configuration of an observational information table stored in both the administration server and the mobile terminal device in the subject observation system of the embodiment.

A subject observation system in the embodiment watches a subject Ob as a watching target (supervising target) to be observed (supervised) to thereby accomplish observation of the subject Ob, and includes a sensor unit for inspecting and notifying a predetermined movement of the subject Ob, a display device for displaying predetermined information, and a central processing apparatus communicatively connected with the sensor unit and the display device respectively to receive from the sensor unit a transmission of an inspection result about an inspection performed by the sensor unit and transmit the inspection result to the display device.

Specifically, for example, as shown in FIG. 1, a subject observation system MS includes one or more sensor units (inspector units) SU (SU-1 to SU-4), an administration server SV, a stationary terminal device SP and one or more mobile terminal devices TA (TA-1, TA-2), which are communicatively connected with one another via a wired or wireless network NW or communication line, such as a LAN (Local Area Network), a telephone network and a data communication network. The network NW may include a relay device, such as a repeater, bridge, rooter and cross connect, to relay a communication signal. In the embodiment shown in FIG. 1, the sensor units SU-1 to SU-4, the administration server SV, the stationary terminal device SP and the mobile terminal devices TA-1, T1-2 are communicatively connected with one another via a wireless LAN (such as a LAN satisfying IEEE802.11 standard) NW including an access point AP.

As clearly seen from the detailed description below, the sensor unit SU is an exemplary sensor unit, the administration server SV is an exemplary central processing apparatus, and each of the stationary terminal device SP and the mobile terminal device TA is an exemplary display device.

The subject observation system MS is disposed at a location suitable for the subject Ob. The subject (supervising target) Ob may involve, for example, a person who requires nursing due to an illness or injury, a person who needs care due to reduction in the physical ability, and a person living alone. Particularly, the subject Ob is appreciated to require finding of a predetermined inconvenient incident, for example, an abnormality condition, happened to the subject in terms of achievement in early finding and quick action. For this reason, the subject observation system MS is preferably disposed in a building, such as a hospital, a welfare facility for the elderly and a house, depending on a type of the subject Ob. In the embodiment shown in FIG. 1, the subject observation system MS is disposed in a care facility building provided with a plurality of chambers including resident rooms RM respectively for a plurality of subjects Ob to live therein, a nurse station, and other rooms.

Each of the sensor units SU has a communication function to communicate with the other devices SV, SP, TA via the network NW, and serves as a device for inspecting a predetermined movement of the subject Ob, and sending an inspection result about the inspection to the administration server SV. Specifically, the sensor unit SU is, for example, composed of: a communication interface circuit, such as an LAN card or the like, to communicate with the other devices SV, SP, TA via the network NW; an image sensor for photographing the subject Ob and generating an image; a data processing circuit for determining a state (condition) of the subject Ob as an inspection result of the subject Ob in connection with an output (image) from the image sensor; a control circuit for controlling all the aforementioned elements; and peripheral circuits therearound. The sensor unit SU sends the inspection result to the administration server SV. The sensor unit SU sends the generated image (including a still image and a video image) to the predetermined other devices SV, SP, TA.

Specifically, in the embodiment, the predetermined movement involves, for example, a waking-up movement, a leaving movement from a bed, falling over, and falling down of the subject Ob. The sensor unit SU inspects the waking-up movement, the leaving movement from the bed, the falling over, and the falling down of the subject Ob by a well-known technology on the basis of an image generated by photographing the subject Ob. For example, the sensor unit SU extracts a moving body region as a person body region of the subject Ob from an image generated by photographing the subject Ob by means of a background subtraction way or a frame subtraction way, determines a posture (such as standing, sitting and lying) of the subject Ob from an aspect ratio of the extracted moving body region, detects a position in the extracted moving body region, distinctively judges the waking up, the leaving movement from the bed, the falling down, and the falling over on the basis of the extracted, detected and determined posture and position of the subject Ob. Specifically, the sensor unit SU sequentially determines respective postures of lying, sitting and standing as an aspect ratio of a laterally long image comes into smaller aspect ratios. The waking-up is judged when the subject staying over sleeping equipment such as a bed changes in the posture from a lying posture to a sitting posture; the leaving movement from a bed is judged when the subject changes in the posture from the sleeping equipment to an outside of the sleeping equipment in a standing state; the falling down is judged when the subject is in a lying posture around the sleeping equipment; or the falling over is judged when the subject is in a lying posture at a position away from the sleeping equipment. Further, upon inspection of the predetermined movement of the subject Ob, the sensor unit SU sends to the administration server SV a communication signal (event notification communication signal) which contains inspected movement information representing a type of the inspected movement (at least one of the waking-up movement, the leaving movement from the bed, the falling over and the falling down in the embodiment), an event time at which the predetermined movement is inspected, a sensor ID of the sensor unit SU and a still image (or, for example, the last image of a plurality of images subjected to the inspection) used for the inspection. A sensor unit identifier (sensor ID) is an identified to specify and identify the sensor unit SU.

The sensor unit SU further includes a nurse call circuit for sending a nurse call to the stationary terminal device SP and the mobile terminal device TA, and a communication circuit for performing a voice communication with the stationary terminal device SP and the mobile terminal device TA, which thus enables nurse calling and a voice communication.

As an example, an embodiment shown in FIG. 1 includes first through fourth sensor units SU-1 through SU-4. The first sensor unit SU-1 is arranged in an unillustrated resident room RM-1 of a resident A, i.e., subject Ob-1, who is one of the subjects Ob, the second sensor unit SU-2 is arranged in an unillustrated resident room RM-2 of another resident B, i.e., subject Ob-2, who is another one of the subjects Ob, the third sensor unit SU-3 is arranged in an unillustrated resident room RM-3 of further another resident C, i.e., subject Ob-3, who is further another one of the subjects Ob, and the fourth sensor unit SU-4 is arranged in an illustrated resident room RM-4 of sill further another resident D, i.e., subject Ob-4, who is one of the subjects Ob.

The administration server SV has a communication function or the like to communicate with the other devices SU, SP, TA via the network NW, and serves as a device for administrating the entirety of the subject observation system MS by: receiving an event notification communication signal from the sensor SU and administrating information (observational information) about observation of the subject Ob; transmitting (retransmitting, transferring, sending) the received event notification communication signal to a predetermined terminal device SP, TA; controlling a display of the observational information to be displayed on the terminal device (stationary terminal device, mobile terminal device) SP, TA; and providing data to a client (terminal device SP, TA, or the like in the embodiment) in response to a request from the client. As shown in FIG. 2, the administration server SV includes, for example, a server communication interface section (SV communication IF section) 21, a server control processing section (SV control processing section) 22, and a server storage section (SV storage section) 23.

The SV communication IF section 21 is connected to the SV control processing section 22, and serves as a circuit for performing a communication in accordance with a control of the SV control processing section 22. The SV communication IF section 21 generates a communication signal containing data input from the SV control processing section 22 for transfer in accordance with a communication protocol used in the network NW of the subject observation system MS, and sends the generated communication signal to the other devices SU, SP, TA via the network NW. The SV communication IF section 21 receives a communication signal from the other devices SU, SP, TA via the network NW, takes data from the received signal, converts the taken data to another one having a different format that can be processed by the SV control processing section 22, and outputs the converted data to the SV control processing section 22. The SV communication IF section 21 includes a communication interface circuit satisfying, for example, the IEEE 802.11 standard.

The SV storage section 23 is connected to the SV control processing section 22, and serves as a circuit for storing various predetermined programs and data. For example, the various predetermined programs include control processing programs such as an SV control program for controlling respective parts of the administration server SV in accordance with their functions, and an SV observational processing program for executing a predetermined process about the observation of the subject Ob. The various predetermined data contains data necessary for executing the programs, such as a server identifier (server ID) of the administration server SV for specifying and identifying the administration server SV, observational information about the observation of the subject Ob, inter-device information representing an association between devices such as a transmission destination of the event notification communication signal, and sensor unit information about the sensor unit SU. The SV storage section 23 is operably provided with a server observational information storage part (SV observational information storage part) 231, an inter-device information storage part 232 and a server sensor unit information storage part (SV sensor unit information storage part) 233 for respectively storing the observational information, the inter-device information and the sensor unit information respectively.

The SV observational information storage part 231 stores the observational information about the observation of the subject Ob. In the embodiment, the observational information includes: a movement type (event type, that is, the waking-up movement, the leaving movement from the bed, the falling over, or the falling down in the embodiment) based on the inspected movement information, an event time, a sensor ID, and a still image, respectively contained in the event notification communication signal; a communication address (such as an IP address) of the sensor unit SU as an acquisition destination for a live video image; and action information indicating whether or not an intention of doing an action (execution, reply), such as lifesaving, nursing, care and help, to the subject Ob is input to the mobile terminal device TA. The SV observational information storage part 231 stores the information in association with one another. In this case, a receipt time of the event notification communication signal may be appreciated to be adopted in place of the event time.

In the embodiment, the SV observational information storage part 231 stores the observational information in a table format. As shown in FIG. 4, an observational information table MT-SV where the observational information is registered, for example, includes: a sensor ID field 51-SV for registering the sensor ID; an event type field 52-SV for registering the event type in connection with the sensor unit SU having the sensor ID registered in the sensor ID field 51-SV; an event time field 53-SV for registering the event time in connection with the sensor unit SU having the sensor ID registered in the sensor ID field 51-SV; a still image field 54-SV for registering the still image in connection with the sensor unit SU having the sensor ID registered in the sensor ID field 51-SV; a video image field 55-SV for registering a communication address (such as an IP address) of the sensor unit SU having the sensor ID registered in the sensor ID field 51-SV as an acquisition destination for a live video image; and an action field 56-SV for registering the action information indicating an input or non-input of an intention of an action (action intention, execution intention, reply intention) to the subject Ob being inspected by the sensor unit SU having the sensor ID registered in the sensor field 51-SV, and further has a record per receipt of an event notification communication signal. Registered in the action field 56-SV is a flag representing the action information indicating the input or non-input of the intention of the action. In the embodiment, registered in the action field 56-SV is, for example, a flag "1" representing an input of the intention of the action to the mobile terminal device TA, or a flag "0" representing no input of the intention of the action to the mobile terminal device TA. When a new record is generated upon receipt of another event notification communication signal, registered in the action field 56-SV is "0" as a default value. In this case, in the still image field 54-SV, it is appreciated to register, for example, image data of the still image, and further a file name of the image data of the still image. FIG. 4 shows an example where a first record represents "SU-1", "waking-up movement", "06:32", "SP1", "..." (here, it should be noted that denoted at the sign "**" is an integer value)", and "0" registered respectively in the fields 51-SV to 56-SV.

Furthermore, in the example shown in FIG. 4, an observational information table MT-SV includes the video image field 55-SV. However, it is appreciated to store another table in the SV observational information storage part 231 in advance in addition to the observational information table MT-SV, another table showing an associative relationship between the sensor ID and the communication address of the sensor unit SU as an acquisition destination for a live video image. In this case, the video image field 55-SV may be excluded from the observational information table MT-SV shown in FIG. 4.

Moreover, as described in detail later, the mobile terminal device TA also contains a similar observational information table MT-TA in order to store observational information. Therefore, FIG. 4 shows reference numerals and signs for the observational information table MT-TA as well.

The inter-device information storage part 232 stores in advance the inter-device information representing an association between the devices, such as a transmission destination of the event notification communication signal. In the embodiment, the inter-device information storage part 232 stores, as the inter-device information, an associative relationship (transmission destination associative relationship) between a sensor ID which is a sending source of an event notification communication signal and a terminal ID which is a transmission destination (retransmission destination, transfer destination, sending destination) of the event notification communication signal, and an associative relationship (communication address associative relationship) between an ID (sensor ID, terminal ID) of each of the devices SU, SP, TA and a communication address thereof. The terminal ID is a terminal identifier to specify and identify each of the terminal devices SP, TA. In this configuration, each of the sensor ID, the server ID and the terminal ID may be made up by, for example, a serial number composed of a predetermined symbol string, or by a communication address (in this case, the communication address associative relationship may be omitted).

The SV sensor unit information storage part 233 stores the sensor unit information about the sensor unit SU in advance. In the embodiment, the SV sensor unit information storage part 233 stores, as the sensor unit information, an associative relationship among a sensor ID, information (arrangement location information) representing an arrangement location of a sensor unit SU having the sensor ID, and a name of the subject being inspected by the sensor unit SU having the sensor ID.

The SV control processing section 22 serves as a circuit for administrating the entirety of the subject observation system MS by: controlling respective parts of the administration server SV in accordance with their functions; receiving an event notification communication signal from the sensor unit SU and administrating the observational information about the observation of the subject Ob; transmitting the received event notification communication signal to a predetermined terminal device SP, TA; and providing data to a client (terminal device SP, TA, or the like in the embodiment) in response to a request from the client. The SV control processing section 22 includes, for example, a CPU and peripheral circuits therearound. The SV control processing section 22 is operably provided with a server control part (SV control part) 221 and a server observation processing part (SV observation processing part) 222 owing to execution of the control processing programs.

The SV control part 221 controls the respective parts of the administration server SV in accordance with their functions to thereby control the entirety of the administration server SV.

Upon receipt of an event notification communication signal from the sensor unit SU, the SV observation processing part 222 causes the SV observational information storage part 231 to store (record) the observational information about the observation of the subject Ob, selects (searches) from the transmission destination associative relationship stored in the inter-device information storage part 232 a transmission destination (retransmission destination, transfer destination, sending destination) corresponding to the sensor unit SU having transmitted the received event notification communication signal, and sends the event notification communication signal to a selected terminal device SP, TA. The selection (search process) is performed on the basis of the sensor ID corresponding to the sensor unit SU having sent the received event notification communication signal. In this case, the event notification communication signal to be retransmitted contains a communication address corresponding to the sensor unit SU having sent the received event notification communication signal as a download destination for a video image. The communication address is selected (searched) from the communication address associative relationship on the basis of the sensor ID corresponding to the sensor unit SU having sent the received event notification communication signal. The SV observation processing part 222 sends to the mobile terminal device TA the sensor unit information stored in the SV sensor unit information storage part 233 by a communication signal containing the information. The sending of the sensor unit information is, for example, performed when the mobile terminal device TA is logged in, which will be described later. Then, when the SV communication IF section 21 receives from the terminal device SP, TA an action notification communication signal serving as a communication signal of notifying the subject Ob that an action intention has been received, the SV observation processing part 222 causes the SV observational information storage part 231 to store an acceptance of the action intention, and the SV communication IF section 21 sends an action unnecessary notification communication signal serving as a communication signal of suspending a display of the inspection result of the subject Ob to whom the action intention directs by means of simultaneous transmission. The simultaneous transmission may be, for example, a broad cast for sending the action unnecessary notification communication signal to all the terminal devices SP, TA in the subject observation system MS, or a multicast for sending the action unnecessary notification communication signal to a plurality of predetermined terminal devices SP, TA in the subject observation system MS.

As shown by the dashed line in FIG. 2, the administration server SV may be appreciated to include, for example, a server input part (SV input part) 24 for inputting various commands and data, a server output part (SV output part) 25 for outputting the various commands and data input by the SV input part 24 and information about the observation of the subject Ob and the like, and a server interface part (SVIF part) 26 for performing the input and output of the data in cooperation with the external devices, the parts 24, 25 and 26 being connected to the SV control processing section 22.

The administration server SV may be made up by, for example, a computer having a communication function.

The stationary terminal device SP has a communication function to communicate with the other devices SU, SV, TA via the network NW, a display function to display predetermined information, and an input function to input a predetermined instruction or predetermined data, and further serves as a user interface (UI) of the subject observation system MS by inputting the predetermined instruction or data to be given to the administration server SV or the mobile terminal device TA, displaying the observational information obtained at the sensor unit SU and the like. For example, the stationary terminal device SP may be made up by a computer having a communication function. Here, the stationary device SP, which is a terminal device, can work in a similar manner to the mobile terminal device TA. In the specification, the terminal device will be exemplarily described with reference to the mobile terminal device TA which is a terminal device.

The mobile terminal device TA has a communication function to communicate with the other devices SV, SP, SU via the network NW, a display function to display predetermined information, an input function to input a predetermined instruction or predetermined data, and a talking function to perform a voice communication, and serves as a device for receiving and displaying the observational information about the observation of the subject Ob by inputting the predetermined instruction or data to be given to the administration server SV or the sensor unit SU, displaying the observational information (including a video image) obtained by the sensor unit SU by means of a transmission from the administration server SV, and performing a voice communication with the sensor unit SU. In the embodiment, as shown in FIG. 3, the mobile terminal device TA includes, for example, a terminal communication interface section (TA communication IF section) 31, a terminal control processing section (TA control processing section) 32, a terminal storage section (TA storage section) 33, a terminal sound input and output part (TA sound input and output part) 34, a terminal input part (TA input part) 35, a terminal display part (TA display part) 36, and a terminal interface part (TAIF part) 37.

The TA sound input and output part 34 is connected to the TA control processing section 32, and serves as a device for acquiring an external sound and inputting the acquired sound into the mobile terminal device TA, and further generating and outputting a sound corresponding to a sound representative electric signal in accordance with control by the TA control processing section 32. The TA sound input and output part 34 includes, for example, a microphone to convert a sound acoustic vibration to the electric signal, and a speaker to convert a sound electric signal to a sound acoustic vibration, and other elements. The TA sound input and output part 34 outputs an external sound representative electric signal to the TA control processing section 32, and converts the electric signal input from the TA control processing section 32 to the sound acoustic vibration to thereby output the converted sound acoustic vibration.

The TA input part 35 is connected to the TA control processing section 32, and serves as a device, such as a plurality of switches allotted with predetermined functions, for accepting a predetermined operation and inputting it into the mobile terminal device TA. The predetermined operation involves various operations necessary for the observation, for example, an operation of inputting an ID for logging in, another operations of requesting and finishing a voice communication, further another operations of requesting and finishing a live video image, and a still further another operation of inputting an intention of doing the action ("acting"), such as lifesaving, nursing, care and help, to the notified subject Ob. The TA display part 36 is connected to the TA control processing section 32, and serves as a display device, such as an LCD (Liquid Crystal Display) and an organic EL display, for displaying contents of the predetermined operation input from the TA input part 35 and the observational information about the subject Ob (for example, a classified predetermined movement having been inspected by the sensor unit SU, or an image, such as a still image or a video image, of the subject Ob) observed by the subject observation system MS. Besides, in the embodiment, the TA input part 35 and the TA display part 36 constitute a touch panel. In this case, the TA input part 35 is a positional input device which effects an input by detecting an operated position in a resistive membrane way or electrostatic capacity way, for example. The touch panel provides the positional input device over the display screen of the TA display part 36. The TA display part 36 displays one or more inputtable candidate contents. For example, when a user (observer) such as a nurse or a caregiver touches a position displaying an input content which the user wants to input, the positional input device detects the touched position, and the content displayed at the detected position is input to the mobile terminal device TA as an input content operated by the user.

The TAIF part 37 is connected to the TA control processing section 32, and serves as a device for inputting and outputting data with an external device in accordance with a control of the TA control processing section 32, i.e., an interface circuit adopting the Bluetooth (Registered Trademark) standard, the IrDA standard used for infrared communication, or the USB standard, or the like.

Like the SV communication IF section 21, the TA communication IF section 31 is connected to the TA control processing section 32, and serves as a communication device for performing a communication in accordance with a control of the TA control processing section 32. The TA communication IF section 31 generates a communication signal containing the data input from the TA control processing section 32 for transfer in accordance with a communication protocol used in the network NW of the subject observation system MS, and sends the generated communication signal to the other devices SU, SV, SP via the network NW. The TA communication IF section 31 receives a communication signal from the devices SU, SV, SP via the network NW, takes data from the received communication signal, converts the taken data to another one having a different format that can be processed by the TA control processing section 32, and outputs the converted data to the TA control processing section 32. The TA communication IF section 31 include, for example, a communication interface circuit satisfying the IEEE802.11 standard.

The TA storage section 33 is connected to the TA control processing section 32, and serves as a circuit for storing various predetermined programs and data in accordance with a control of the TA control processing section 32. The various predetermined programs include, for example, control processing programs such as a TA control program for controlling the respective parts of the mobile terminal device TA in accordance with their functions, a TA observational processing program for executing a predetermined process about the observation of the subject Ob, a TA voice communication processing program for performing a voice communication with the sensor unit SU by using the TA sound input and output part 34, and a TA streaming processing program for receiving a distribution of a video image from the sensor unit SU and causing the TA display part 36 to display the video image received through the distribution by means of streaming reproduction. The TA observational processing program further involves a display processing program for causing the TA display part 36 to display a screen image suitable for respective information contained in a retransmitted event notification communication signal as a predetermined process about the observation of the subject Ob upon receipt of the retransmitted event notification communication signal from the administration server SV. Each predetermined data includes data necessary for executing the respective programs, such as a terminal ID of the terminal device TA, display screen image information to be displayed on the TA display part 36, the observational information about the observation of the subject Ob, and the sensor unit information about the sensor unit SU. The TA storage section 33 includes, for example, a ROM and an EEPROM. The TA storage section 33 further includes a RAM or the like serving as a working memory of the TA control processing section 32 to store data generated during execution of the predetermined programs. The TA storage section 33 is operably provided with a display screen image storage part 331, a terminal observational information storage part (TA observational information storage part) 332, and a terminal sensor unit information storage part 333 for respectively storing the display screen image information, the observational information, and the sensor unit information.

The display screen image storage part 331 stores an image, such as a display screen image, to be displayed on the TA display part 36 in accordance with a control of a display processor 3221 of the TA control processing section 32 to be described later, and is, for example, a VRAM (video memory). When there are a plurality of observational information screen images representing respective observational information about a plurality of subjects Ob as described later, the display screen image storage part 331 stores the observational information screen images in association with each other in a predetermined order. The TA display part 36 is appreciated to display the observational information screen images by selectively changing the observational information screen images one after another in response to an input operation (change operation) received by the TA input part 35 for changing a display content (display screen image), the observational information screen images being associated with each other in the predetermined order. Alternatively, the TA display part 36 may be made to display the observational information screen images by shifting from one after another while continuously displaying them, in response to a change operation received by the TA input part 35. Specifically, in the embodiment, upon receipt of event notification communication signals respectively in connection with a plurality of subjects Ob who are different from each other, observational information screen images corresponding to the plurality of event notification communication signals are connected with each other in the predetermined order to thereby form a plane. Specifically, in the embodiment, the observational information screen images are, for example, vertically connected with each other in the predetermined order when they are displayed on the TA display part 36 to thereby form the plane, or may be laterally connected instead of the vertical connection manner. Normally, an observational information screen image has a plane size which is to be stored in the display screen image storage part 331 and equivalent to a size of a screen image display region of the TA display part 36. In contrast, upon receipt of a plurality of event notification communication signals, an observational information screen image corresponding to each of the event notification communication signals has the normal plane size, and the observational information screen images respectively corresponding to the event notification communication signals are connected with each other in the predetermined order to thereby form a plane. Thus, the size of the plane formed upon receipt of the plurality of event notification communication signals changes in accordance with the number of the observational information screen images. Owing to the control of the display processor 3221 in the TA observation processing part 322, the TA display part 36 displays only a part of the plane having a size that is equivalent to the size of the screen image display region of the TA display part 36 among the plurality of observational information screen images forming the plane. Moreover, the TA display part 36 further displays on the screen being displayed thereon a new arrival observational information indication serving as a code representing a presence of observational information in connection with a new event notification communication signal having been received.

The TA observational information storage part 332 stores the observational information about the observation of the subject Ob, and stores the observational information similar to that stored in the SV observational information storage part 231 in a table format, that is, an observational information table MT-TA having the same configuration as that of the SV observational information storage part 231, as shown in FIG. 4.

The TA sensor unit information storage part 333 stores the sensor unit information about the sensor unit SU in advance, specifically, receives the sensor unit information from the administration server SV to thereby store the same in the same manner as the SV sensor unit information storage part 233.

The TA control processing section 32 serves as a circuit for controlling respective parts of the terminal device TA in accordance with their functions, and receiving and displaying the observational information about the observation of the subject Ob. Like the SV control processing section 22, the TA control processing section 32 includes, for example, a CPU and periphery circuits therearound. Owing to execution of the control processing programs, the TA control processing section 32 is operably provided with a terminal control part (TA control part) 321, a terminal observation processing part (TA observation processing part) 322, a terminal voice communication processing part (TA voice communication processing part) 323, and a terminal streaming processing part 324. The TA observation processing part 322 is further operably provided with the display processor 3221.

The TA control part 321 controls the respective parts of the mobile terminal device TA in accordance with their functions to thereby control the entirety of the mobile terminal device TA.

The TA observation processing part 322 executes a predetermined process about the observation of the subject Ob. Specifically, upon receipt of a retransmitted event notification communication signal from the administration server SV, the TA observation processing part 322 causes the TA observational information storage part 332 to store (record) the observational information about the observation of the subject Ob on the basis of the information (data) contained in the received event notification communication signal. Further, upon receipt of a predetermined input operation by the TA input part 35, the TA observation processing part 322 executes a predetermined process in response to the input operation. Specifically, for example, upon receipt of the change instruction by the TA input part 35, the TA observation processing part 322 causes the display processor 3221 to render the TA display part 36 to display an observational information screen image in response to the change instruction. Moreover, for example, upon receipt of an input operation of inputting to the mobile terminal device TA an intention of doing an actual action ("acting"), such as lifesaving, nursing, care and help, to the subject Ob (i.e., upon receipt of the action intension), the TA observation processing part 322 causes the display processor 3221 to allow an action notification communication signal serving as a communication signal of notifying the subject Ob that the action intention has been received to be transmitted to the other terminal devices SP, TA via the administration server SV. Also, for example, upon receipt of an input operation of requesting a voice communication by the TA input part 35, the TA observation processing part 322 causes the TA voice communication processing part 323 to request a voice communication to the sensor unit SU, thereby achieving the voice communication therewith. After that, upon receipt of an input operation of finishing the voice communication by the TA input part 35, the TA observation processing part 322 causes the TA voice communication processing part 323 to request finish of the voice communication to the sensor unit SU, thereby finishing the voice communication therewith. Furthermore, for example, upon receipt of an input operation of requesting a live video image by the TA input part 35, the TA observation processing part 322 causes the TA streaming processing part 324 to request a distribution of the video image to the sensor unit SU, and renders the TA display part 36 to display the video image. Then, upon receipt of an input operation of finishing the distribution of the live video image by the TA input part 35, the TA observation processing part 322 causes the TA streaming processing part 324 to request suspending the distribution of the video image to the sensor unit SU, and renders the TA display part 36 to finish the display of the video image.

Upon receipt of a retransmitted event notification communication signal from the administration server SV, the display processor 3221 renders the TA display part 36 to display a screen image corresponding to each information contained in the retransmitted event notification communicational signal in accordance with a predetermined process. Specifically, when there is one observational information screen image representing observational information about one subject Ob, the display processor 3221 renders the display screen image storage part 331 to store the one observational information screen image, and renders the TA display part 36 to display the same. In contrast, when there are plurality of observational information screen images representing observational information respectively about a plurality of subjects Ob, the display processor 3221 renders the display screen image storage part 331 to store the observational information screen images in association with each other in a predetermined order, and renders the TA display part 36 to display a predetermined one of the observational information screen images. Specifically, in the embodiment, the display processor 3221 connects the observational information screen images with each other in the predetermined order to thereby form a plane, renders the display screen image storage part 331 to store the resultant plane, and renders the TA display part 36 to display predetermined one of the observational information screen images. More specifically, the display processor 3221 renders the TA display part 36 to display a new arrival observation information indication (for example, a double circle mark 532, i.e. "⊚532", see FIG. 6) serving as a code representing a presence of observational information in connection with a new event notification communication signal upon receipt of a transmission of the new event notification communication signal via the TA communication IF section 31, while maintaining an existing display content being displayed on the TA display part 36, and to further display the observational information of the received new event notification communication signal upon receipt of the change instruction by the TA input part 35. Preferably, upon receipt of the change instruction by the TA input part 35, the display processor 3221 renders the TA display part 36 to display the observational information of the received new event notification communication after displaying all pieces of observational information in connection with the plurality of event notification communication signals having been previously received between the existing display content and the observational information in connection with the received new event notification communication signal. When the TA display part 36 displays the observational information in connection with the received new event notification communication signal, the display processor 3221 deletes the new arrival observational information indication 532 from the TA display part 36 in such a manner as to keep the TA display part 36 from displaying the new arrival observational information indication 532. Upon receipt of the action intention by the TA input part 35, the display processor 3221 keeps the TA display part 36 from displaying the observational information of the subject Ob to whom the action intention directs. The display processor 3221 allows the TA communication IF section 31 to send to the administration server SV an action notification communication signal serving as a communication signal of notifying the subject Ob that the action intention has been received upon receipt of the action intention by the TA input part 35, and further keeps the TA display part 36 from displaying the observational information of the subject Ob in connection with an action unnecessary notification communication signal serving as a communication signal of suspending the display of the observational information of the subject Ob to whom the action intention directs upon receipt of the action unnecessary notification communication signal. In the embodiment, the predetermined order is appreciated to be a chronological order, and the display processor 3221 can sequentially change the screen images in the chronological order.

The TA voice communication processing part 323 performs the voice communication with the sensor unit SU by using the TA sound input and output part 34 by means of, for example, VoIP (Voice over Internet Protocol).

The TA streaming processing part 324 receives a distribution of a video image from the sensor unit SU, and causes the TA display part 36 to display the video image received through the distribution by means of the streaming reproduction.

The mobile terminal device TA may be made up by a portable communication terminal device such as a tablet computer, a smart phone and a mobile phone.

Next, operations performed in the embodiment will be described. A subject observation system MS having the above-described configuration includes respective devices SU, SV, SP, TA which initialize necessary parts thereof and then activate when the power is turned on. An administration server SV includes an SV control processing section 22 operably provided with an SV control part 221 and an SV observation processing part 222 owing to execution of control processing programs thereof. A mobile terminal device TA includes a TA control processing section 32 operably provided with a TA control part 321, a TA observation processing part 322, a TA voice communication processing part 323, and a TA streaming processing part 324 owing to execution of control processing programs thereof. The TA observation processing part 322 is operably provided with a display processor 3221.

Briefly, the subject observation system MS having the above-described configuration observes each subject Ob by the following operations. A sensor unit SU takes outputs of an image at a predetermined sampling cycle, inspects a state (condition) of the subject Ob on the basis of the taken outputs respectively, and, when determining that the subject Ob is in a predetermined state (such as the waking-up movement, the leaving movement from the bed, the falling over, and the falling down in the embodiment) as a result of the inspection, sends to the administration server SV an event notification communication signal in connection with inspected movement information.

When the administration server SV receives an event notification communication signal from the sensor unit US, the SV observation processing part 222 of the SV control processing section 22 renders an SV observational information storage part 231 to store (record) observational information about observation of a subject Ob on the basis of the received event notification communication signal, selects (searches) from a transmission destination associative relationship stored in an inter-device information storage part 232 a transmission destination (retransmission destination, transfer destination, sending destination) corresponding to the sensor unit SU having sent the received event notification communication signal, and further renders the SV communication IF section 21 to send (retransmit) the event notification communication signal to a selected terminal device SP, TA. In this manner, the state (condition) of the subject Ob is notified to, for example, a nurse or a caregiver via the terminal device SP, TA.

Upon receipt of the retransmitted event notification communication signal from the administration server SV, each of the stationary terminal device SP and the mobile terminal device TA stores (records) the observational information about the observation of the subject Ob on the basis of the retransmitted event notification communication signal having been received, and displays a screen image (observational information screen image) based on information contained in the retransmitted event notification communication signal having been received, in accordance with a predetermined process. An operation of the mobile terminal device TA for displaying the screen image will be described in detail below. Briefly, the subject observation system MS inspects the subject Ob through the operation by the sensor unit SU, the administration server SV, the stationary terminal device SP and the mobile terminal device TA to thereby accomplish observation of the subject Ob.

Figure 5:
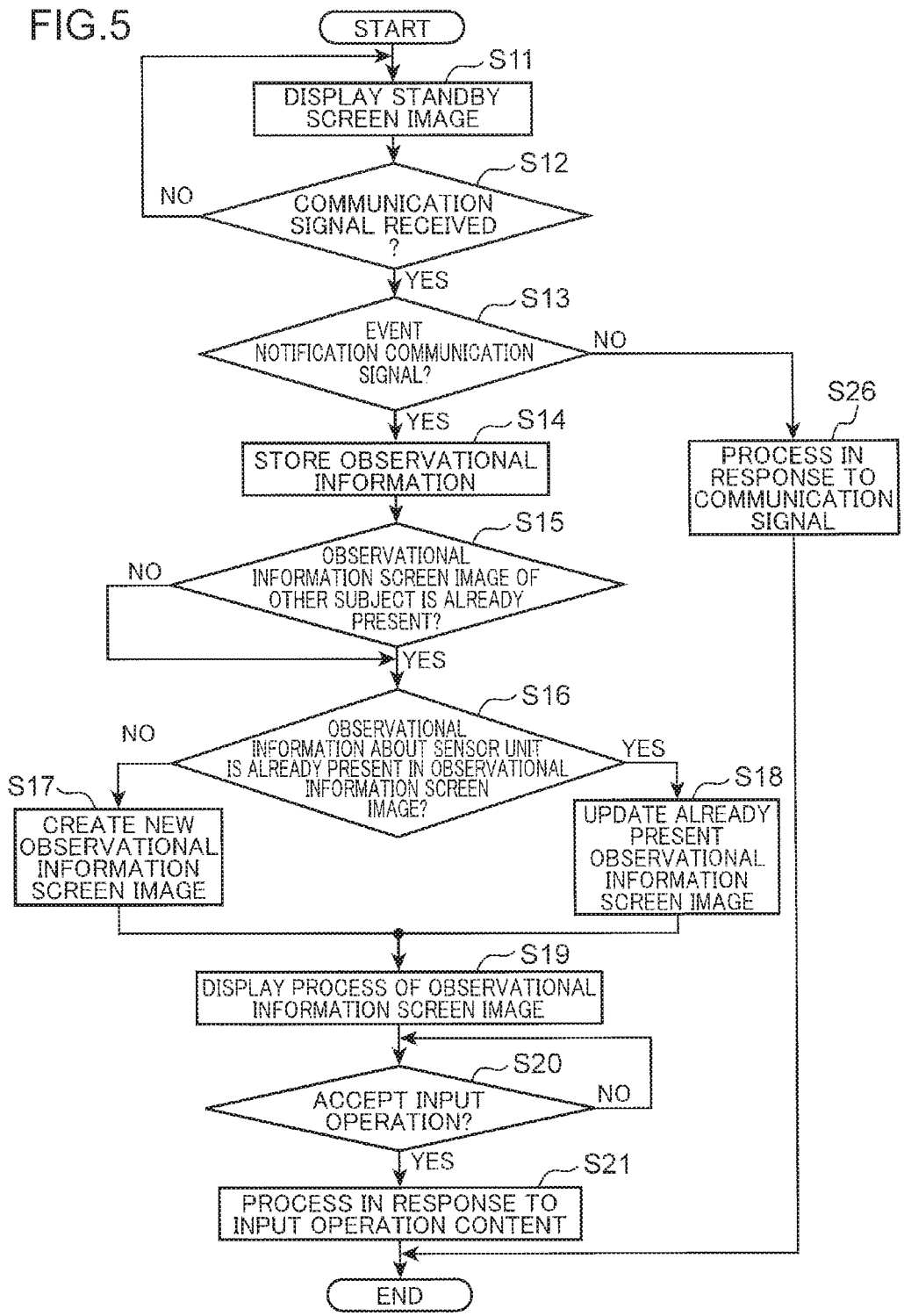
FIG. 5 is a flowchart showing an operation of the mobile terminal device for a transmission of an inspection result in the subject observation system.
Figure 6:
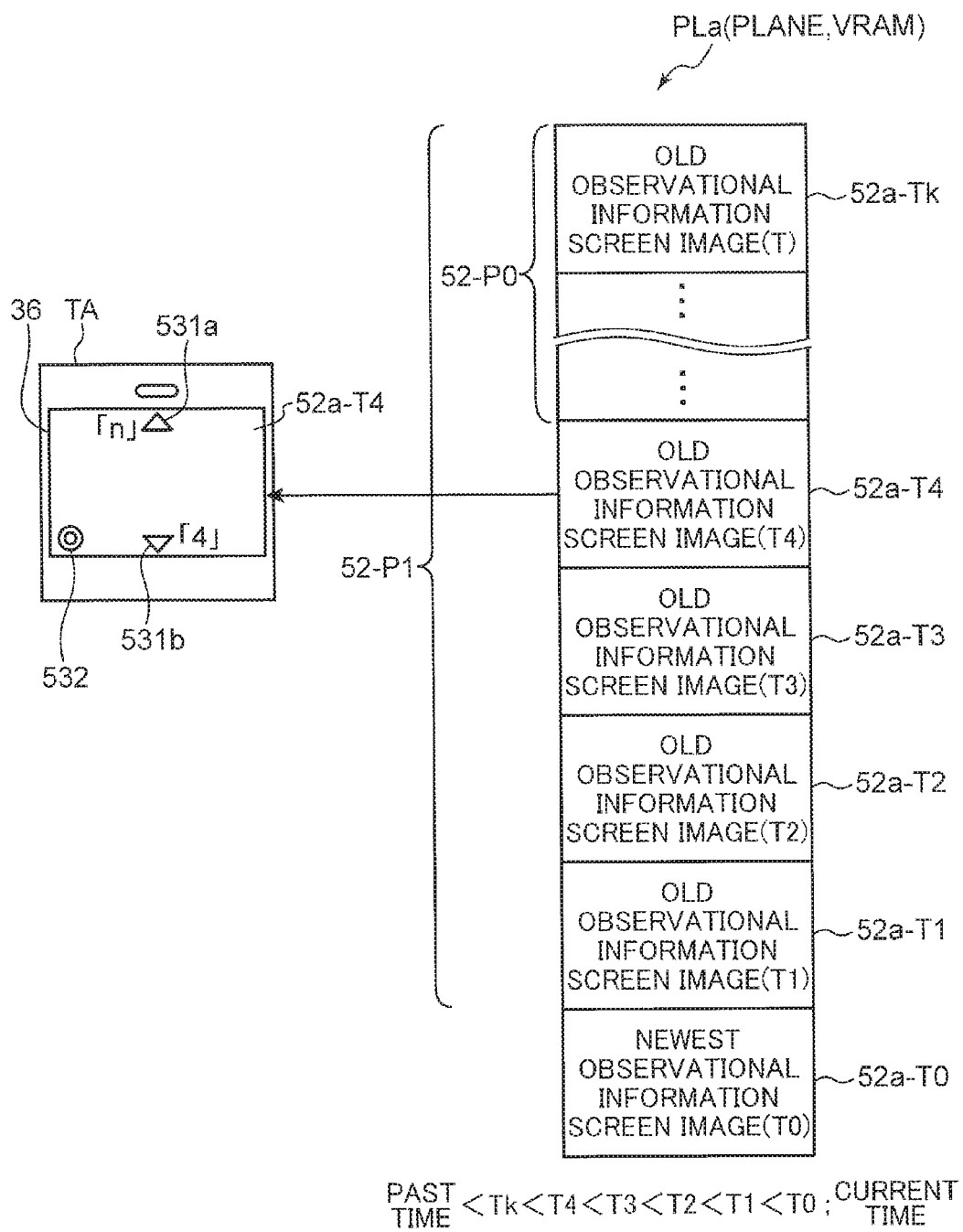
FIG. 6 is a diagram illustrating a first storage way to be executed in a display screen image storage part of the mobile terminal device in the subject observation system.
Figure 8:
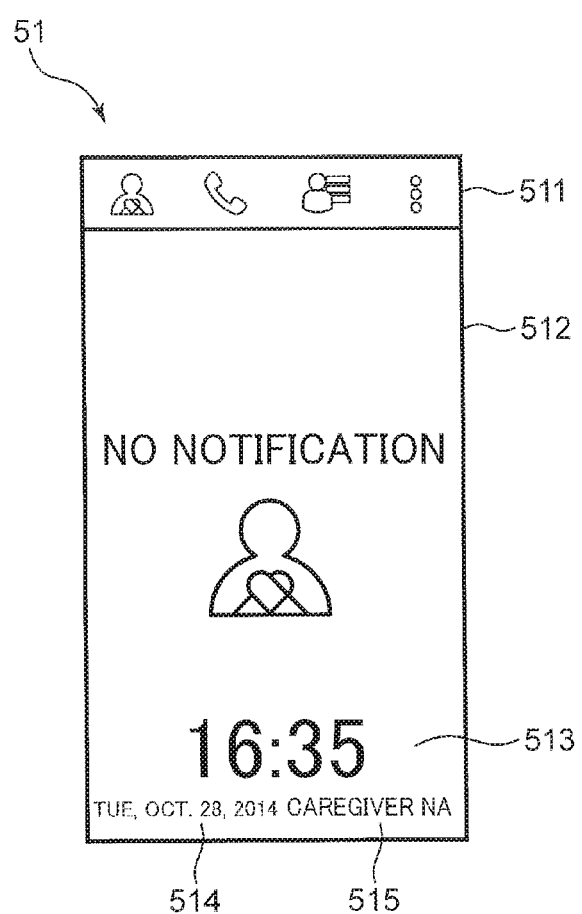
FIG. 8 shows an exemplary standby screen image to be displayed on the mobile terminal device in the subject observation system.
Figure 9:
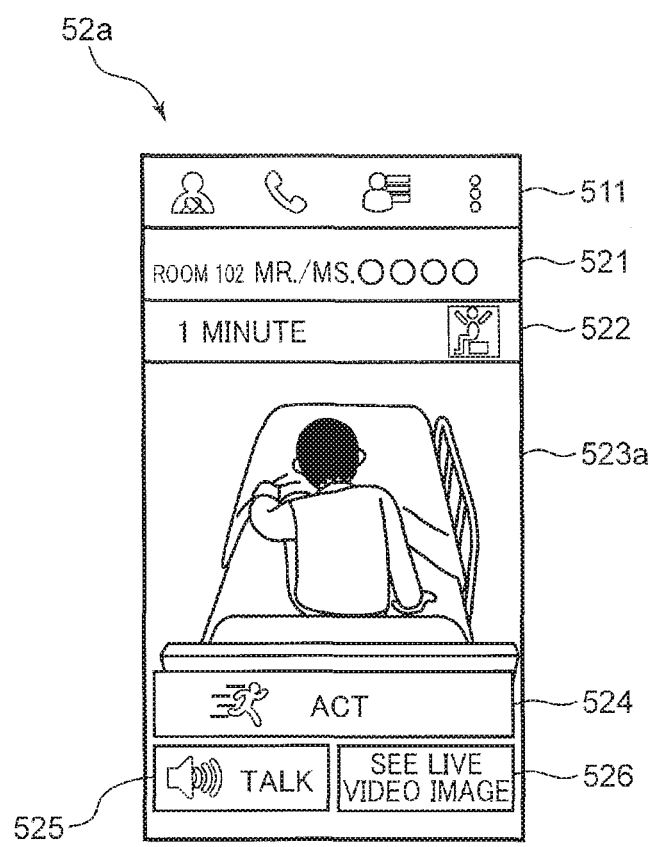
FIG. 9 shows an exemplary still observational information screen image to be displayed on the mobile terminal device in the subject observation system.
Figure 10:
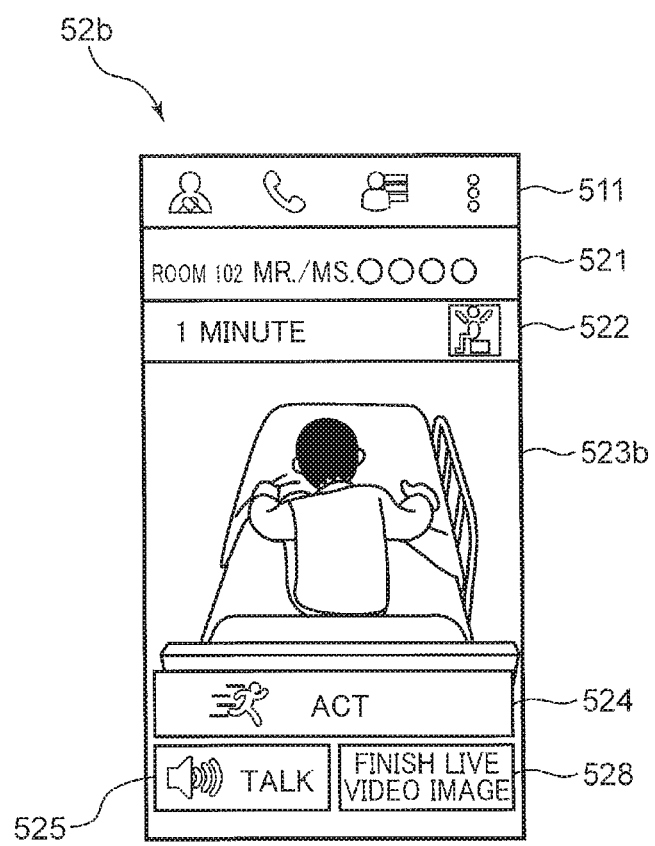
FIG. 10 shows an exemplary motion observational information screen image to be displayed on the mobile terminal device in the subject observation system.
Figure 11A:
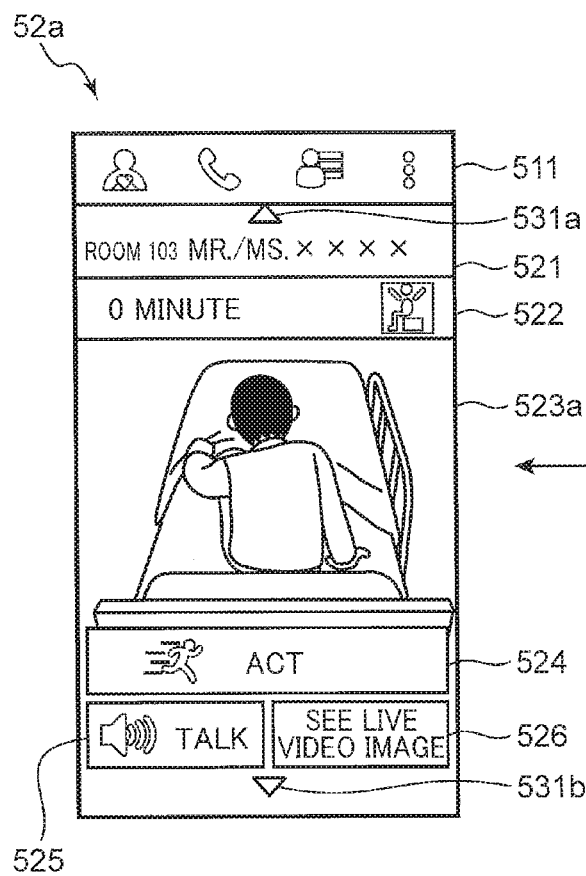
FIG. 11 shows an exemplary observational information screen image to be displayed on the mobile terminal device having received transmissions from two or more sensor units which are different from each other.
Figure 11B:
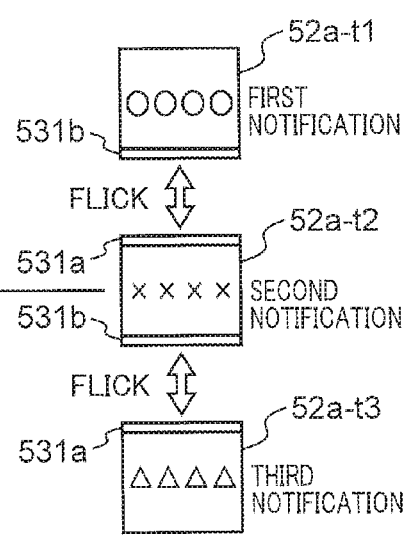

Subsequently, an operation of the mobile terminal device TA for displaying a screen image in the subject observation system MS will be described. FIG. 5 is a flowchart showing an operation of the mobile terminal device for a transmission of an inspection result in the subject observation system of the embodiment. FIG. 6 is a diagram illustrating a first storage way to be executed in a display screen image storage part of the mobile terminal device in the subject observation system of the embodiment. FIG. 7 is a flowchart showing an operation for deleting an observational information screen image in the subject observation system of the embodiment. FIG. 7A shows an operation for deleting an observational information screen image in the administration server SV, and FIG. 7B shows an operation for deleting an observational information screen image in the mobile terminal device TA. FIG. 8 shows an exemplary standby screen image to be displayed on the mobile terminal device in the subject observation system of the embodiment. FIG. 9 shows an exemplary still observational information screen image to be displayed on the mobile terminal device in the subject observation system of the embodiment. FIG. 10 shows an exemplary motion observational information screen image to be displayed on the mobile terminal device in the subject observation system of the embodiment. FIG. 11 shows an exemplary observational information screen image to be displayed on the mobile terminal device having received transmissions from two or more sensor units which are different from each other.

In FIG. 5, the mobile terminal device TA activates when the power is turned on. For example, when the mobile terminal device TA accepts a log-in operation by an observer (user) such as a nurse or a caregiver, the display processor 3221 of the TA observation processing part 322 renders a TA display part 36 to display a standby screen image indicating a standby for receiving a communication signal (step S11) directed to the mobile terminal device TA. As shown in FIG. 8, a standby screen image 51 includes, for example, a menu bar region 511 for displaying a menu bar, a standby main region 512 for displaying a message (for example, "no notification") representing the standby and an icon, a time region 513 for displaying a current time, a calendar region 514 for displaying a day of the week, a date, a month, and a year of today, and a user name region 515 for displaying a name of a user who is logging in the mobile terminal device TA.

Then, the mobile terminal device TA causes a TA control part 321 to judge whether or not a TA communication IF section 31 receives a communication signal (S12) directed to the mobile terminal device TA. The mobile terminal device TA returns the process to step S11 when it is judged that the communication signal directed thereto is not received (No), or proceeds to subsequent step S13 when it is judged that the communication signal directed thereto is received (Yes).

In the step S13, upon receipt of the communication signal directed to the mobile terminal device TA, the mobile terminal device TA causes the TA observation processing part 322 to determine whether or not the received communication signal is an event notification communication signal. The mobile terminal device TA causes the TA control processing section 32 to execute an appropriate process (each exemplary process shown in FIG. 7B to be described later) in response to the received communication signal (step S26) when it is determined that the received communication is not the event notification communication signal (No), and finishes the operation for displaying the screen image. To the contrary, when it is determined that the received communication signal is the event notification communication signal (Yes), the mobile terminal device TA causes the TA observation processing part 322 to register in an observational information table MT-TA a sensor ID, an event type (movement type based on the inspected movement information, i.e. the waking-up movement, the leaving movement from the bed, the falling over, and the falling down in the embodiment), an event time (or receipt time), image data of a still image (or file name thereof), and a communication address to acquire a video image, respectively contained in the received event notification communication signal, thereby causing a TA observational information storage part 332 to store the registered information in association with one another (step S14), and then proceeds to step S15. During registration of the information in the observational information table MT-TA, the TA observation processing part 322 registers a flag "0" representing a default in an action field 56-TA.

In the step S15, the mobile terminal device TA causes the TA observation processing part 322 to determine whether or not another observational information screen image 52-A (observational information screen image 52a (52b)) is already present, and then proceeds to the next step S16, the another observational information screen image 52-A representing observational information about a subject Ob-A who is different from a subject Ob-B in connection with the observational information contained in the received event notification communication signal. The determination result in this step S15 is used in steps S17, 18 and 19 to be described later, respectively. Specifically, the TA observation processing part 322 judges whether or not a different sensor ID from the sensor ID contained in the received event notification communication signal is registered in a sensor ID field 51-TA of a record which registers a flag "0" in an action field 56-TA, thereby determining whether or not the another observational information screen image 52-A is already present. When it is judged that no different sensor ID from the sensor ID contained in the received event notification communication signal is registered in the sensor ID field 51-TA of the record which registers the flag "0" in the action field 56-TA, it is determined that no another observational information screen image 52-A in connection with the different sensor ID is present (No), and then the mobile terminal device TA proceeds to the subsequent step S16. To the contrary, when it is judged that a different sensor ID from the sensor ID contained in the received event notification communication signal is registered in the sensor ID field 51-TA of the record which registers the flag "0" in the action field 56-TA, it is determined that another observational information screen image 52-A in connection with the different sensor ID is already present (Yes), and then the mobile terminal device TA proceeds to the subsequent step S16.

In the step S16, the mobile terminal device TA causes the TA observation processing part 322 to determine whether or not the observational information contained in the received event notification communication signal is observational information in connection with the sensor unit SU for which an observational information screen image 52a (52b) is already present. Specifically, the TA observation processing part 322 determines whether or not an event notification communication signal containing a sensor ID that is identical to the sensor ID contained in the received event notification communication signal has been previously received (in past) prior to the received event notification communication signal, and the observational information screen image 52a (52b) for the previously received event notification communication signal has been created for display. More specifically, the TA observation processing part 322 determines whether or not a sensor ID that is identical to the sensor ID contained in the received event notification communication signal has been already registered in the sensor ID field 51-TA of the record which registers the flag "0" in the action field 56-T to thereby determine whether or not the sensor ID has been previously received, and an observational information screen image 52a (52b) for the previously received event notification communication signal has been created. When it is determined that no sensor ID that is identical to the sensor ID contained in the received event notification communication signal is registered in the sensor ID field 51-TA of the record which registeres the flag "0" in the action field 56-TA, it is judged that no event notification communication signal having the same sensor ID has been previously received (No), and then the mobile terminal device TA proceeds to step 17. To the contrary, when it is determined that the sensor ID that is identical to the sensor ID contained in the received event notification communication signal is registered in the sensor ID field 51-TA of the record which registers the flag "0" in the action field 56-TA, it is judged that the event notification communication signal having the same sensor ID has been previously received (Yes), and then the mobile terminal device TA proceeds to step S18.

In the step S17, in the mobile terminal device TA, the display processor 3221 of the TA observation processing part 322 creates a new observational information screen image 52a based on the respective information (data) contained in the received event notification communication signal and renders the display screen image storage part 331 to store the created new observation information screen image 52a.

The observational information screen image 52a is a screen image for displaying the observational information about the observation of the subject Ob. As shown in FIG. 9, the observational information screen image 52a includes, for example, a menu bar region 511, a subject name region 521 for displaying an arrangement location of a sensor unit SU having a sensor ID and a name of a subject Ob to be observed by the sensor unit SU having the sensor ID, an icon region 522 for displaying a lapse time period from an event time (or receipt time) and an icon symbolically representing an inspection result represented by the inspected movement information, an image region 523a for displaying an image (here, still image) photographed by the sensor unit SU having the sensor ID, an "act" button 524, a "talk" button 525, and a "see LIVE video image" button 526. The "act" button 524 is used to input information that a user of the mobile terminal device TA has an intention (action intention, execution intention, reply intention) of doing the action (execution, reply) such as lifesaving, nursing, care and help to the subject Ob being inspected by the sensor unit SU having the sensor ID. The "talk" button 525 is used to input a request for a voice communication, and to input an instruction of requesting communicative connection between the sensor unit SU having the sensor ID and the mobile terminal device TA via the network NW. The "see LIVE video image" button 526 is used to input an instruction of displaying a video image photographed by the sensor unit SU having the sensor ID.

In order to create the observational information screen image 52a based on the respective information contained in the received event notification communication signal, the TA display processor 3221 searches an arrangement location corresponding to a sensor ID contained in the received event notification communication signal and a subject name from a TA sensor unit information storage part 333 by using the sensor ID as a search key, obtains a lapse time period from an event time (or receipt time) contained in the received event notification communication signal, and searches an icon corresponding to an inspection result represented by the inspected movement information contained in the received event notification communication signal from the TA storage section 33 by using the inspection result as a search key. It should be noted that icons respectively corresponding to inspection results (the waking-up movement, the leaving movement from the bed, the falling over and the falling down in the embodiment) are stored in the TA storage section 33 in advance in association with the inspection results. Moreover, the display processor 3221 creates the observational information screen image 52a by displaying the menu bar in the menu bar region 511, the searched arrangement location and the subject name in the subject name region 521, the obtained lapse time period and the searched icon in the icon region 522, the image (still image) contained in the received event notification communication signal in the image region 523a, and further displaying the "act" button 524, the "talk" button 525, and the "see LIVE video image" button 625, and then renders the display screen image storage part 331 to store the created observational information screen image 52a.

Moreover, after creation of such a new observational information screen image 52a (52a-B), when it is determined in the step 15 that an observational information screen image 52-A in connection with a different sensor ID is already present, the display processor 3221 renders the display screen image storage part 331 to store the created new observational information screen image 52a-B in association with the already present observational information screen image 52-A in a predetermined order. Specifically, the display processor 3221 vertically connects the created new observational information screen image 52a-B to the already present observational information screen image 52-A in a chronological order when they are displayed on the TA display part 36 to thereby form a plane.

Returning to FIG. 5, in the mobile terminal device TA, the display processor 3221 of the TA observation processing part 322 updates, in the step S18, the observational information screen image 52a (52a-B) on the basis of the respective information (data) contained in the received event notification communication signal, and renders the display screen image storage part 331 to store the updated observational information screen image.

In order to update an observational information screen image 52a-B on the basis of the respective information contained in the received event notification communication signal, the display processor 3221 obtains a lapse time period from an event time (or receipt time) contained in the received event notification communication signal, and searches an icon corresponding to an inspection result represented by the inspected movement information contained in the received event notification communication signal from the TA storage section 33 by using the inspection result as a search key. Besides, the display processor 3221 updates (creates) the observational information screen image 52a-B, and renders the display screen image storage part 331 to store the updated (created) observational information screen image 52a-B by displaying the obtained lapse time period and the searched icon in the icon region 522, and the image (still image) contained in the received event notification signal in the image region 523a onto an already present observational information screen image 52a-B. Here, the icon region 522 includes already displayed icons corresponding to inspection results contained in the received event notification communication signal. Thus, the currently searched icon is displayed next to the already displayed icons in a chronological order in the icon region 522. For example, when an inspection result "leaving movement from the bed" of the subject Ob is notified after another inspection result "waking up movement" of the subject Ob, as shown in FIG. 9, the observational information screen image 52a where an icon representing the inspection result "waking-up movement" of the subject Ob is displayed in the icon region 522 is updated by displaying the icon representing the inspection result "leaving movement from the bed" of the subject Ob to the left of the icon representing the inspection result "waking-up movement" in the icon region 522 on the paper.

Subsequently, like the step S17, upon update or creation of the observational information screen image 52a-B, when it is determined in the step S15 that an observational information screen image 52-A in connection with a different sensor ID is already present, the display processor 3221 renders the display screen image storage part 331 to store the updated or created new observational information screen image 52a-B and the already present observational information screen image 52-A in association with each other in the predetermined order. Specifically, the display processor 3221 vertically connects the updated or created observational information screen image 52a-B to the already present observational information screen image 52-A in a chronological order when they are displayed on the TA display part 36 to thereby form a plane. In this case, the display processor 3221 is appreciated to maintain an existing chronological relationship (chronological connection) to associate the screen images with each other in the chronological order, or reorganize the screen images to associate them with each other in a new chronological order based on the received event notification communication signal.

Subsequent to the step S17 or S18, the display processor 3221 executes a predetermined process to display an observational information screen image 52a (S19). Specifically, when it is determined in the step S15 that no observational information screen image 52-A in connection with a different sensor ID is present (that is, when only one observational screen image 52a is present as a result of the step S17 or S18), the display processor 3221 renders the TA display part 36 to display a new observational information screen image 52a having been created in the step S17 or a latest observational information screen image 52a having been updated in the step S18. To the contrary, when it is determined in the step S15 that the observational information screen image 52-A in connection with the different sensor ID is present (that is, when a plurality of observational information screen images 52a representing the observational information respectively about a plurality of subjects Ob who are different from each other are present), the display processor 3221 renders the TA display part 36 to further display a new arrival observational information indication 532 to an existing display content, while maintaining the existing display content being displayed thereon.

In an embodiment shown in FIG. 6, in a state that a plurality of observational information screen images 52-P1 are present, upon receipt of a new event notification communication signal at a time T0, the mobile terminal device TA proceeds to steps S13, S14, S15, S16 and S17 to thereby create an observational information screen image 52a-T0 corresponding to the received new event notification communication signal, vertically connect the created new observational information screen image 52a-T0 to the already present observational information screen images 52-P1 in a chronological order when they are displayed on the TA display part 36 to thereby form a plane PLa, and cause the display screen image storage part 331 to store the resultant plane PLa. The observational information screen images 52-P1 are formed into a plane by vertically connecting an observational information screen image 52a-T4 obtained at a time T4 in past to a plurality of observational information screen images 52-P0 including observational information screen images 52a-Tk obtained at times Tk in past, an observational information screen image 52a-T3 obtained at a time T3 in past to the observational information screen image 52a-T4, an observational information screen image 52a-T2 obtained at a time T2 in past to the observational information screen image 52a-T3, and an observational information screen image 52a-T1 obtained at a time T1 in past to the observational information screen image 52a-T2 respectively in a chronological order when they are displayed on the TA display part 36. The chronological order can be expressed by "past time<time Tk . . . <time T4<time T3<time T2<time T0<current time". Then, the mobile terminal device TA proceeds to step S19, and renders the TA display part 36 to further display a new arrival observational information indication 532 to an existing display content, while maintaining the display content being displayed thereon. In the embodiment shown in FIG. 6, the TA display part 36 displays the observational information screen image 52a-T4 obtained at the time T4 in past. In the step 19, a display of the new arrival observational information indication 532 is added to the observational information screen image 52a-T4, while the display of the observational information screen image 52a-T4 is maintained.

Next, the mobile terminal device TA causes the TA control processing section 32 to determine whether or not a touch panel constituted by a TA input part 35 and a TA display part 36 accepts an input operation (step S20). The mobile terminal device TA returns the process to the step S20 when it is determined that the input operation is not accepted (No), or proceeds to subsequent step S21 when it is determined that the input operation is accepted (Yes).

In the step S21, the mobile terminal device TA causes the TA control processing section 32 to perform an appropriate process corresponding to contents of the input operation, and then finishes the operation for displaying the screen image.

For example, in the mobile terminal device TA, when the TA control processing section 32 accepts an input operation of the "see LIVE video image" button 526, a TA streaming processing part 324 allows a communication signal (video image distribution request communication signal) containing information including a request for a distribution of a live video image to be sent to the sensor unit SU inspecting the subject Ob being displayed on the TA display part 36, connects the mobile terminal device TA with the sensor unit SU having responded to the communication signal via the network NW to thereby permit downloading of the video image, receives a distribution of the live video image from the sensor unit SU, and renders the TA display part 36 to display the video image received through the distribution by means of streaming reproduction. As shown in FIG. 10, a motion observational information screen image 52b includes, for example, an image region 523b for displaying the video image and a "finish LIVE video image" button 528 respectively in place of the image region 523a for displaying a still image and the "see LIVE video image" button 526 in the observational information screen image 52a of FIG. 9. The "finish LIVE video image" button 528 is used to request finish of the video image, and to input an instruction of finishing (suspending) the distribution of the video image photographed by the sensor unit SU having the sensor ID to thereby finish (suspend) the display.

Further, in the mobile terminal device TA, for example, when the TA control processing section 32 accepts an input operation of the "finish LIVE video image" button 528, the TA streaming processing part 324 allows a communication signal (video image distribution finish communication signal) containing information including the request for the finish of the distribution of the video image to be sent to the sensor unit SU inspecting the subject Ob being displayed on the TA display part 36, and renders the TA display part 36 to display a still observational information screen image 52a.

For example, in the mobile terminal device TA, when the TA control processing section 32 accepts an input operation of the "talk" button 525, the TA voice communication processing part 323 allows a communication signal (talking request communication signal) containing information including a request for a voice communication to be sent to the sensor unit SU inspecting the subject Ob being displayed on the TA display part 36 in such a manner that the mobile terminal device TA is voice-communicatively connected with the sensor unit SU having responded to the communication signal via the network NW. In this manner, a voice communication is available between the mobile terminal device TA and the sensor unit SU.

Moreover, for example, in the mobile terminal device TA, when the TA control processing section 32 accepts an input operation of an unillustrated "finish" button to input an instruction of finishing the voice communication, the TA voice communication processing part 323 allows a communication signal (talk finish communication signal) containing information including the request for finish of the voice communication to be sent to the sensor unit SU inspecting the subject Ob being displayed on the TA display part 36.

Furthermore, for example, in the mobile terminal device TA, upon acceptance of an input operation of the "act" button 524 (that is, acceptance of the action intention), the TA control processing section 32 registers a flag "1" in an action field 56-TA in a record which currently registers a sensor ID corresponding to observational information of a subject Ob being displayed on a TA display part 36 in a sensor ID field 51-TA. Moreover, the display processor 3221 keeps the TA display part 36 from displaying the observational information of the subject Ob. Specifically, the display processor 3221 keeps the TA display part 36 from displaying the observational information of the subject Ob by deleting the observational information screen image 52a showing the observational information of the subject Ob from the display screen image storage part 331. More specifically, when only the observational information screen image 52a showing the observational information of the subject Ob is present, the display processor 3221 deletes the observational information screen image 52a from the display image storage part 331, and renders the TA display part 36 to display a standby screen image 51. In contrast, when a plurality of observational information screen images 52a are present, the display processor 3221 deletes the aforementioned observational information screen image 52a from the display screen image storage part 331, and vertically connects the remaining observational information screen images 52a in a chronological order when they are displayed on the TA display part 36 to thereby form a plane, renders the display screen image storage part 331 to store the resultant plane, and further renders the TA display part 36 to display a predetermined observational information screen image 52a. For example, the TA display part 36 displays an observational information screen image 52a which is the most chronologically approximate to the deleted observational information screen image 52a (i.e., an observational information screen image 52a in connection with an event notification communication signal received immediately after the creation of the deleted observational information screen image 52a, or another observational information screen image 52a in connection with another event notification communication signal received just before the creation of the deleted observational information screen image 52a). Alternatively, for example, the TA display part 36 displays another observational information screen image 52a in connection with the oldest event notification communication signal received in past among the remaining observational information screen images 52a. Alternatively, for example, the TA display part 36 displays further another observational information screen image 52a in connection with the newest event notification communication signal currently received among the remaining observational information screen images 52a. Then, the display processor 3221 sends to the administration server SV a communication signal (action notification communication signal) of notifying the subject Ob in connection with the deleted observational information screen image 52a that an observer (user) logging in the mobile terminal device TA has an intention (action intention) of doing an action, such as nursing or the like, and that the action intention has been received. The action notification communication signal contains information (action intention receipt information) indicating that the action intention has been received, a sensor ID corresponding to the observational information in connection with the deleted observational information screen image 52a as information representing a subject to whom the action is directed, and a terminal ID of the mobile terminal device TA as information representing a person who does the action. The terminal ID is acquired from the TA storage section 33.

Besides, for example, in the mobile terminal device TA, when the TA control processing section 32 accepts an input operation of a "flick" performed in a predetermined direction over the touch panel constituted by the TA input part 35 and the TA display part 36, the display processor 3221 enables a display of an observational information screen image 52 corresponding to another observational information screen image indication 531 at a flick source by shifting the display thereto. The "flick" is an exemplary change instruction input. The another observational information screen image indication 531 (531a, 531b) represents a presence of an observational information screen image 52a-B in addition to an observational information screen image 52a-A being displayed on the TA display part 36, and is denoted by, for example, a triangle mark ($\Delta$531a, $\nabla$531b) as shown in an embodiment in FIG. 11. For example, when the "flick" is performed from an upper position to a lower position on a display screen of the TA display part 36, the observational information screen image 52a-B corresponding to the another observational information screen image indication 531 at the flick source is displayed after the display of the observational information screen image 52a-A being displayed is shifted to the display of the observational information screen image 52a-B. Specifically, as shown in FIG. 11, for example, in a case that a plurality of observational information screen images 52a in connection with event notification communication signals having been received are present, and contain a second observational information screen image 52a-t1 obtained at a time earlier than a first observational information screen image 52a-t2, the display processor 3221 renders the display screen image storage part 331 to store the first observational information screen image 52a-t2 and the second observational information screen image 52a-t1 in association with each other in a chronological order, and further to store the first observational information screen image 52a-t2 and a third observational information screen image 52a-t3 obtained at a time later than the second observational information screen image 52a-t2 in association with each other in the chronological order in the case of the presence of the third observational information screen image 52a-t3. Also, the display processor 3221 renders the TA display part 36 to display a first another observational information screen indication 531a representing the presence of the second observational information screen image 52a-t1 at one end (upper end in an embodiment shown in FIG. 11) of the first observational information screen image 52a-t2, and a second another observational information screen image indication 531*b* representing the presence of the third observational information screen image 52*a*-*t*3 at the other end (lower end in the embodiment shown in FIG. 11) of the first observational information screen image 52*a*-*t*2 while displaying the first observational information screen image 52*a*-*t*2, and further to display an observational information screen image 52*a* corresponding to the another observational information screen indication 531 (531*a*, 531*b*) at the flick source by shifting the display thereto in response to the input operation of the "flick". Specifically, in response to a first flick performed in one direction from a lower position to an upper position over the touch panel, the display processor 3221 renders the TA display part 36 to display the third observational information screen image 52*a*-*t*3 by shifting the display from the first observational information screen image 52*a*-*t*2 being displayed on the TA display part 36 thereto in order to change the screen images in a forward direction from an older screen image to a newer screen image. To the contrary, in response to a second flick performed in another direction opposite to the one direction from an upper position to a lower position over the touch panel, the display processor 3221 renders the TA display part 36 to display the second observational information screen image 52*a*-*t*1 by shifting the display from the first observational information screen image 52*a*-*t*2 being displayed on the TA display part 36 thereto in order to change the screen images in a backward direction from a newer screen image to an older screen image. As described above, in the embodiment, the display screen image storage part 331 stores the plurality of observational information screen images 52*a* in association with each other in the chronological order. In this configuration, the TA display part 36 can sequentially display a plurality of inspection results in a forward direction from an older inspection result to a newer inspection result or in a backward direction from a newer inspection result to an older inspection result by a flick operation.

Furthermore, for example, in the embodiment shown in FIG. 6, when the TA display part 36 of the mobile terminal device TA displays an old observational information screen image 52*a*-T4 including a new arrival observational information indication 532, a first flick is performed in one direction from a lower position to an upper position over the touch panel in order to display a newest observational information screen image 52*a*-T0 in connection with the new arrival observational information indication 532. In response to the first flick, the screen images are sequentially shifted in the forward direction from an older observational information screen image to a newer observational information screen image, i.e., in the order of an old observational information 52*a*-T4 being displayed to an old observational information screen image 52*a*-T3, an old observational information screen image 52*a*-T2, and an old observational information screen image 52*a*-T1. After that, the TA display part 36 displays the newest observational information screen image 52*a*-T0, and the new arrival observational information indication 532 is deleted from the TA display part 36. In this manner, the TA display part 36 displays the newest observational information screen image 52*a*-T0 in connection with the received new event notification communication signal after displaying all the plurality of observational information screen images 52*a*-T3 to 52*a*-T1 in connection with corresponding event notification communication signals having been previously received between the old observational information screen image 52*a*-T4 and the newest observational information screen image 52*a*-T0.

Hereinafter, an operation of the mobile terminal device TA for deleting a screen display image in the subject observation system will be described.

In FIG. 7A, in the administration server SV, when the SV control part 221 causes the SV communication IF section 21 to receive a communication signal (step S31) directed to the administration server SV, an SV observation processing part 222 determines a type of the received communication signal (step S32). The administration sever SV proceeds to step S33 when it is determined that the received communication signal is an action notification communication signal (action notification), proceeds to step S34 when it is determined that the received communication signal is not the action notification communication signal (, but is other signal).

In the step 33, in the administration sever SV, the SV observation processing part 222 registers a fag "1" in an action field 56-SV in a record which registers a sensor ID contained in the received action notification communication signal in a sensor ID field 51-SV, and causes the SV communication IF section 21 to send, by means of a simultaneous communication, an action unnecessary notification communication signal serving as a communication signal of suspending a display of observational information about a subject Ob to whom an action intention directs by the action notification communication signal having been received in the step 31, and then finishes the operation for deleting the display screen image. In order to specify an observational information screen image 52*a* (52*b*) to be deleted, the action unnecessary notification communication signal contains a sensor ID contained in the action notification communication signal having been received in the step 31, information (a command, observational information screen image deletion instruction information, an observational information screen image deletion command) representing an instruction (command, order) for deleting an observational information screen image 52*a* (52*b*) in connection with a sensor unit SU corresponding to the sensor ID, and action intention receipt information for registration of the flag "1" in the action field 56-SV of the terminal device SP, TA having received the observational information screen image deletion communication signal.

In the step S34, the administration server SV causes the SV control processing section 22 to execute an appropriate process in response to each received communication signal, and finishes the operation for deleting the display screen image.

A mobile terminal device TA having received the action unnecessary notification communication performs the following operation.

In an example of step S26 shown in FIG. 5, the mobile terminal device TA causes the TA observational processing part 322 to determine a type of the received communication (S41). The mobile terminal device TA proceeds to step S42 when it is determined that the received communication signal is an action unnecessary notification communication signal (which means that an action is unnecessary), and proceeds to step S43 when it is determined that the received communication signal is not the action unnecessary notification communication (, but is other signal).

In the step S42, the mobile terminal device TA, first, causes the TA observation processing part 322 to determine whether or not an observational information screen image 52*a* (52*b*) in connection with a sensor unit SU having a sensor ID contained in the received action unnecessary notification communication signal is present. When it is determined that the observational information screen image 52*a* (52*b*) is not present, the TA observation processing part 322 finishes the operation for deleting the display screen image. To the contrary, when it is determined that the observational information screen image 52a (52b) is present, the TA observation processing part 322 registers a flag "1" in the action field 56-TA in a record which registers the sensor ID contained in the received action unnecessary notification communication signal in the sensor ID field 51-TA, and keeps the TA display part 36 from displaying observational information of a subject Ob in connection with the received action unnecessary notification communication signal. Specifically, like the above-described case of acceptance of the "act" button 524, the display processor 3221 keeps the TA display part 36 from displaying the observational information of the subject Ob by deleing the observational information screen image 52a (52b) in connection with the sensor unit SU having the sensor ID contained in the received action unnecessary notification communication signal from the display screen image storage part 331 of the TA storage section 33. In a case that the display screen image storage part 331 stores a plurality of observational information screen images 52a (52b), due to the deletion of the aforementioned observational information screen image 52a (52b), observational information screen images 52a having been respectively created before and after the deleted observational information screen image 52a (52b) are connected with each other. In this manner, the observational information screen image 52a (52b) for which the "act" button 524 has been received is deleted from the mobile terminal device TA. Further, the TA display part 36 suspends the display of the observational information of the subject Ob in connection with the action unnecessary notification communication signal. Then, the display processor 3221 finishes the operation of deleting the display screen image.

In the step S43, the mobile terminal device TA causes the TA control processing section 32 to execute an appropriate process in response to each received communication signal, and finishes the operation for deleting the display screen image.

As described above, in a subject observation system MS, and a terminal device SP, TA which is an exemplary display device as described above, and a method for use in the system in the embodiment, when a sensor unit SU inspects a predetermined movement of a subject Ob, the mobile terminal device TA receives, for example, a transmission of a new inspection result from the sensor unit SU via an administration server SV which is an exemplary central processing apparatus. In this case, a display processor 3221 renders a TA display part 36 to display a new arrival observational information indication 532 as an exemplary code representing a presence of the received new inspection result, while maintaining an existing display content being displayed on the TA display part 36, and further to display the received new inspection result when a TA input part 35 receives a "flick" which is an exemplary change instruction input. In this way, the TA display part 36 displays the exiting display content preferentially to the received new inspection result. Thus, the subject observation system MS, the terminal device SP, TA, and the method for use in the system in the embodiment make it possible to ensure encouragement of an action (execution, reply) to a patient or the like in connection with a previous notification. Moreover, since the TA display part 36 further displays the new arrival observational information indication 532 representing the presence of the received new inspection result, while maintaining the display of the existing display content, a user such as an observer can, for example, recognize the presence of the received new inspection result.

In order to achieve an object of encouraging an observer to act (execute, reply) to a subject Ob when a predetermined incident occurs to the subject Ob, the subject observation system MS inspects, transmits, and displays a predetermined movement of the subject Ob. In the subject observation system MS, the terminal device SP, TA, and the method for use in the system, the display processor 3221, for example, operates as described above in response to receipt of the action intention through an input operation of the "act" button 524 by the TA input part 35. This operation makes it possible to keep the TA display part 36 from displaying the inspection result of the subject Ob to whom the action intention directs, the inspection result no more requiring the display owing to the achievement of the aforementioned object.

In the subject observation system MS, the terminal device SP, TA, and the method for use in the system, upon receipt of the action intention through the input operation of the "act" button 524 by the TA input part 35 of at least any one of the plurality of mobile terminal devices TA, it is possible to keep the TA display part 36 from displaying an inspection result of the subject Ob to whom the action intention directs, the inspection result no more requiring the display in all the terminal devices SP, TA owing to the achievement of the aforementioned object, and further coordinate (cooperate) the terminal devices SP, TA with each other for non-display of the inspection result by sending and receiving the action notification communication signal.

Moreover, in the embodiment, in a case that a plurality of event notification communication signals are received, and a plurality of pending observational screen images 52a for which no action intension has been received are present, the terminal device SP, TA may be made to display a total number (i.e., a total case number) of observational screen images 52a including an observational information screen image 52a being displayed, or a total number (i.e., a total number of standbys) of the observational screen images 52a excluding the observational information screen image 52a being displayed. For example, in the mobile terminal device TA, the display processor 3221 renders the TA display part 36 to display the number of standbys of observational information screen images 52a leading to a first another observational information screen image indication 531a in a position closer to the first another observational information screen image indication 531a over an observational information screen image 52a being displayed, and to display the number of standbys of observational information screen images 52a leading to a second another observational information screen image indication 531b in a position closer to the second another observational information screen image indication 531b over the observational information screen image 52a being displayed. For example, in the embodiment shown in FIG. 6, the display processor 3221 renders the display part 36 to display the number of standbys "4" in the position closer to the second another observational information screen image indication 531b.

Additionally, in the embodiment, one sensor unit SU (sensor ID) is allotted with one observational information screen image 52a. Thus, a single observational information screen image 52a is prepared for event notification communication signals sent from the same sensor unit SU (sensor ID), since it can be updated upon receipt of each of the event notification communication signals. However, a plurality of observational information screen images 52a may be respectively created for the event notification communication signals to thereby form a plane in a chronological order, and the display screen image storage part 331 may store the resultant plane. In this case, the process proceeds to the step S19 through the steps S15 and S17 in place of the steps S16 and S18.

Figure 12:
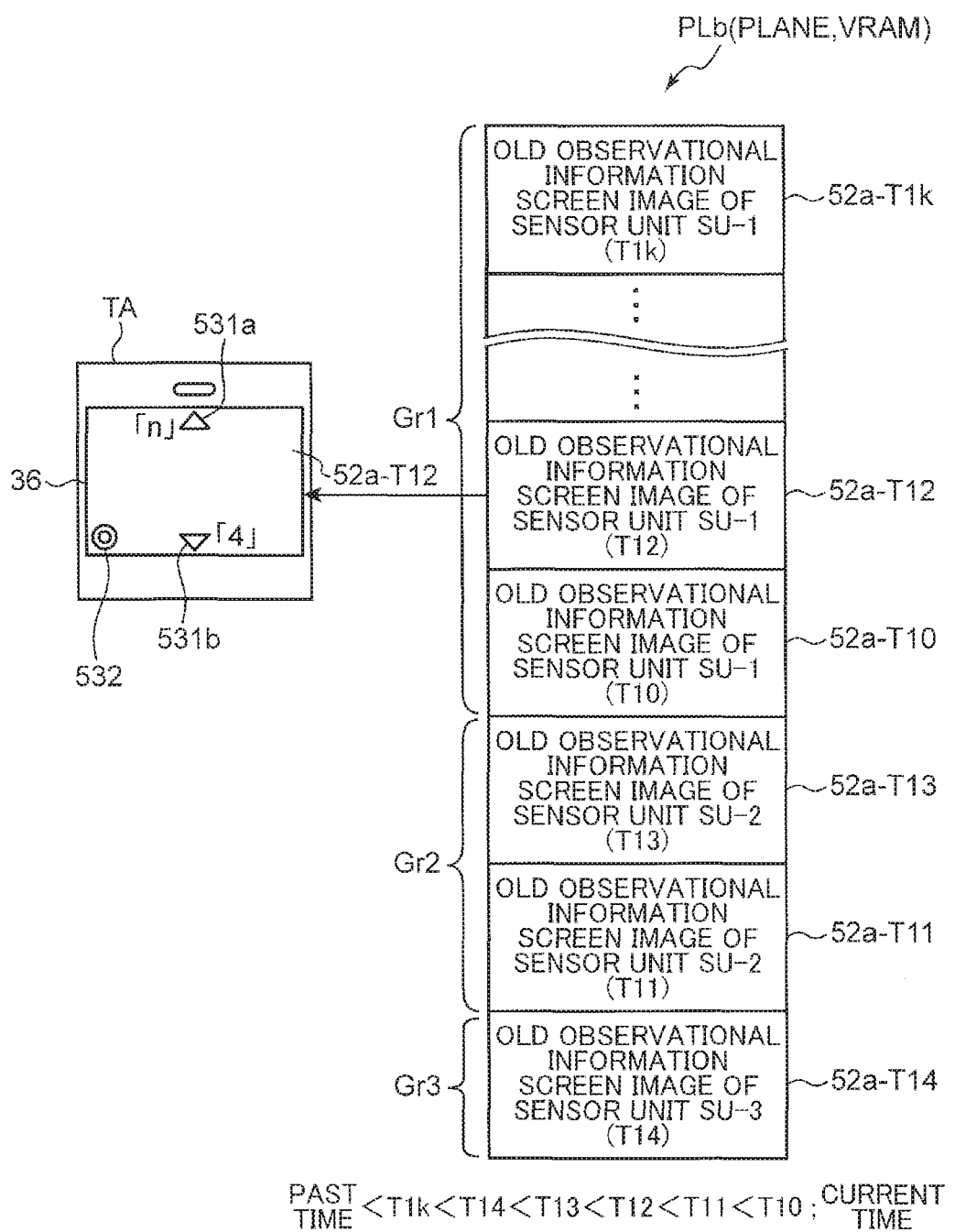
FIG. 12 is a diagram illustrating a second storage way to be executed in the display screen image storage part of the mobile terminal device in the subject observation system.

FIG. 12 is a view illustrating a second storage way to be executed in the display screen image storage part of the mobile terminal device in the subject observation system of the embodiment. FIG. 13 is a diagram illustrating a third storage way to be executed in the display screen image storage part of the mobile terminal device in the subject observation system of the embodiment.

In this case, the observational information screen images 52a may be chronologically connected in a event time order (or receipt time order) to thereby form a plane, the display screen image storage part 331 may store the resultant plane, and the TA display part 36 may display the same in the chronological order in response to the change instruction ("flick" in the embodiment) received by the TA input part 35. Here, the ways of forming and displaying the plane are not limited thereto, and can be appropriately modified.

For example, as shown in FIG. 12, upon receipt of transmissions of observational information by event notification communication signals respectively from a plurality of sensor units SU via an administration server SV, a display processor 3221 may sort a plurality of observational information screen images 52a based on the observational information into groups Gr in accordance with the sensor units SU having corresponding sensor IDs, connect the observational information screen images 52a in accordance with the groups Gr, and further connects the groups Gr with each other to thereby form a plane PLb, render the display screen image storage part 331 to store the resultant plane PLb, and render the TA display part 36 to sequentially display the same in accordance with the groups Gr in response to the change instruction ("flick" in the embodiment") received by the TA input part 35. Furthermore, preferably, the observational information screen images 52a are connected with each other in the chronological order in each of the groups Gr. This configuration allows the TA display part 36 to sequentially display a plurality of pieces of observational information in accordance with the sensor units SU, and thus makes it possible to refer to the observational information corresponding to a subject Ob being inspected by each of the sensor units SU.

In an embodiment shown in FIG. 12, a plane PLb including a plurality of observational screen images 52a-T1k, . . . , 52a-T14 to 52a-T10 and stored in the display screen image storage part 331 is formed by connecting a first group Gr1, a second group Gr2 and a third group Gr3 with one another in a predetermined order (for example, in an order of numbers allotted to sensor units SU in advance), the first group Gr1 being composed of the observational information screen images 52a-T1k, . . . , 52a-T12, 52a-T10 in connection with event notification communication signals sent from a first sensor unit SU-1 via the administration server SV, the second group Gr2 being composed of the observational information screen images 52a-T13, 52a-T11 in connection with event notification communication signals sent from a second sensor unit SU-2 via the administration server SV, and the third group Gr3 being composed of the observational information screen image 52a-T14 in connection with an event notification communication signal sent from a third sensor unit SU-3 via the administration server SV. Also, the observational information screen images 52a are connected with each other in the chronological order in each of the groups Gr1 to Gr3. The chronological order can be expressed by "past time<time T1k . . . <time T14<time T13<time T12<time T10<current time". Moreover, upon receipt of a notification of a new event notification communication signal via a TA communication IF section 31, the display processor 3221 renders the TA display part 36 to further display a new arrival observational information indication 532 to an existing display content, while maintaining the existing display content being displayed thereon. In the embodiment shown in FIG. 12, upon receipt of a new event notification communication signal from the sensor unit SU-1 via the administration server SV during a display of the observational information screen image 52a-T12 obtained at a time T12 in past by the first sensor unit SU-1 on the TA display part 36, the display processor 3221 chronologically connects the newest observational information screen image 52a-T10 in connection with the received new event notification communication signal to the existing observational information screen images 52a-T1k, . . . , 52a-T12 in connection with the sensor unit SU-1 in the first group Gr1 to thereby form a plane PLb, renders the display image storage part 331 to store the resultant plane PLb, and further displays a new arrival observational information indication 532 to the observational information screen image 52a-T12, while maintaining the observational information screen image 52a-T12 being displayed.

Moreover, for example, as shown in FIG. 13, upon receipt of transmissions of a plurality of pieces of observational information by a plurality of event notification communication signals via the administration server SV, the display processor 3221 may sort a plurality of observational information screen images 52a respectively based on the observational information into groups Gr in accordance with a predetermined importance order of classified movements, connect the observational information screen images 52a with each other in accordance with the groups Gr, further connect the groups Gr with each other to thereby form a plane PLc, render the display screen image storage part 331 to store the resultant plane PLb, and render the TA display part 36 to sequentially display the same in accordance with the groups Gr in response to a change instruction ("flick" in the embodiment) received by the TA input part 35. Preferably, the observational information screen images 52a are connected with each other in a chronological order in each of the groups Gr. The importance order serves as an indicator representing an importance level of the observational information, and is set in advance for each of the classified movements as described above. An associative relationship between a movement type and an importance value is, for example, stored in the SV storage section 23 of the administration server SV in advance, sent to the mobile terminal device TA from the administration server SV in a logging-in state, and stored in the TA storage section 33 of the mobile terminal device TA in advance. For example, the associative relationship is established by setting an importance level 1 for the falling over and the falling down, an importance level 2 for the leaving movement from the bed as being secondary important next to the importance level 1, and a importance level 3 for the waking-up movement as being important next to the importance level 2 (that is, highest importance; importance level 1>importance level 2>importance level 3). Since the TA display part 36 sequentially displays the plurality of pieces of observational information in accordance with the importance order thereof, and thus this configuration makes it possible to refer to the observational information in accordance therewith.

In an embodiment shown in FIG. 13, a plane PLc including a plurality of observational information screen images 52a-T2k, . . . , 52a-T24 to 52a-T20 and stored in the display screen image part 331 is formed by connecting a first group Gr11, a second group Gr12, and a third group Gr13 with one another in a predetermined order (for example, in an importance order), the first group Gr11 being composed of the observational information screen images 52a-T2k, . . . , 52a-T22, 52a-T20 set to the importance level 1 in connection with event notification communication signals sent from sensor units SU via the administration server SV, a second group Gr12 being composed of the observational information screen images 52a-T23, 52a-T21 set to the importance level 2 in connection with event notification communication signals sent from sensor units SU via the administration server SV, and a third group Gr13 being composed of the observational information screen image 52a-T24 set to the importance level 3 in connection with an event notification communication signal sent from a sensor unit SU via the administration server SV. Besides, the observational information screen images 52a are connected with each other in a chronological order in each of the groups Gr11 to Gr13. The chronological order can be expressed by "past time<time T2k< . . . <time T24<time T23<time T22<time T21<time T20<current time". Upon receipt of a transmission of an event notification communication signal via a TA communication IF section 31, the display processor 3221 renders the TA display part 36 to further display a new arrival observational information indication 532 to an existing display content, while maintaining the existing display content being displayed on the TA display part 36. In the embodiment shown in FIG. 13, upon receipt of a new event notification communication signal from the sensor unit SU via the administration server SV during a display of the observational information screen image 52a-T22 obtained at a time T22 in past and set to the importance level 1, the display processor 3221 chronologically connects the newest observational information screen image 52a-T20 set to the importance level 1 in connection with the received new event notification communication signal to the existing observational information screen images 52a-T2k, . . . , 52a-T22 in the first group Gr11 to thereby form a plane PLc, renders the display screen image storage part 331 to store the resultant plane PLc, and enables a further display of a new arrival observational information indication 532 to the existing observational information screen image 52a-T22, while maintaining the existing observational information screen image 52a-T22 being displayed.

Additionally, for example, the aforementioned groups may be adopted in combination. For example, it may be appreciated to first sort the observational information screen images 52a into groups in accordance with the sensor units SU, and then, further sort the screen images 52a in the groups into other groups in accordance with the importance order. Alternatively, it may be appreciated to first sort the observational information screen images 52a into groups in accordance with an importance order, and then, further sort them, in the groups, into other groups in accordance with the sensor units SU.

Various aspects of technologies are disclosed in this specification as described above. Main technologies among them will be summarized below.

A display device according to one aspect is a display device for use in a subject observation system to display predetermined information, the system including a sensor unit for inspecting and notifying a predetermined movement of a subject to be observed, the display device, and a central processing apparatus communicatively connected with the sensor unit and the display device respectively to receive from the sensor unit a transmission of an inspection result about an inspection performed by the sensor unit and transmit the inspection result to the display device, the display device including: a communicator which performs a communication; a display part which performs a display; an input part which receives a change instruction input for changing a display content being displayed on the display part; a display processor which renders the display part to display the inspection result transmitted from the central processing apparatus, display a code representing a presence of a new inspection result upon receipt of the transmission of the new inspection result via the communicator, while maintaining the existing display content being displayed thereon, and display the new inspection result on the display part when the input part receives the change instruction input. Preferably, upon receipt of a transmission of a new inspection result via a communicator, the display processor renders the display part to display the code representing a presence of the new inspection result having been received, while maintaining the existing display content being displayed thereon, and further display the new inspection result having been received after displaying all the inspection results obtained between the existing display content and the new inspection result having been received.

When the sensor unit inspects a predetermined movement of a subject, the display device receives a transmission of a new inspection result from the sensor unit via the central processing apparatus. In this case, the display processor renders the display part to display the code representing a presence of the received new inspection result, while maintaining the existing display content being displayed on the display part, and further to display the received new inspection result when the input part receives the change instruction input. In this way, the display part displays the exiting display content preferentially to the received new inspection result. Thus, the display device makes it possible to ensure encouragement of an action (execution, reply) to a patient or the like in connection with a previous notification. Moreover, since the display part further displays the code representing the presence of the received new inspection result, while maintaining the display of the existing display content, a user such as an observer can, for example, recognize the presence of the received new inspection result.

In a display device according to another aspect, the input part further receives an input of an action intension of an observer indicating that the observer intends to do an actual action to the subject, and the display processor keeps the display part from displaying the inspection result of the subject to whom the action intension directs when the input part receives the input of the action intension.

In order to achieve an object of encouraging an observer to act (execute, reply) to a subject when a predetermined incident occurs to the subject, the subject observation system inspects, transmits, and displays a predetermined movement of the subject. The display device makes it possible to keep the display part from displaying the inspection result of the subject to whom the action intention directs, the inspection result no more requiring the display owing to the achievement of the aforementioned object.

In a display device according to a further aspect, the input part further receives a further input of an action intension of executing an actual action to the subject, and upon receipt of the input of the action intension by the input part, the display processor renders the communicator to send to the central processing apparatus an action notification communication signal of notifying the subject that the action intension has been received, and upon receipt of an action unnecessary notification communication signal of suspending a display of the inspection result of the subject to whom the action intension directs, the display processor keeps the display part from displaying the inspection result of the subject in connection with the received action unnecessary notification communication signal.

In the display device, upon receipt of the action intention by the input part of at least any one of the plurality of display devices, it is possible to keep the display part from displaying the inspection result of the subject to whom the action intention directs, the inspection result no more requiring the display in all the display devices, and further coordinate (cooperate) the display devices with each other for non-display of the inspection result by sending and receiving the action notification communication signal.

A display device according to still another aspect, the display part and the input part constitute a touch panel, the change instruction input includes a first flick performed in one direction over the touch panel and a second flick performed in another direction opposite to the one direction over the touch panel, and the display processor changes inspection results to be displayed on the display part in a forward direction from an older inspection result to a newer inspection result in response to the first flick to the touch panel, and renders the display part to display the inspection results, and changes inspection results to be displayed on the display part in a backward direction opposite to the forward direction from a newer inspection result to an older inspection result in response to the second flick to the touch panel, and renders the display part to display the inspection results.

In the display device, the display part can sequentially display a plurality of inspection results in the forward direction from an older inspection result to a newer inspection result or in the backward direction from a newer inspection result to an older inspection result by a flick operation.

In a display device according to further another aspect, the display processor receives a transmission of each of inspection results from each of a plurality of sensor units via the central processing apparatus, and sorts the inspection results into groups in accordance with sensor units, and renders the display part to sequentially display the plurality of inspection results in accordance with the groups.

The display device allows the display part to sequentially display a plurality of inspection results in accordance with the sensor units, and thus makes it possible to refer to the inspection result per each subject being inspected by each of the sensor units.

In display device according to still further another aspect, the display processor receives transmissions of a plurality of inspection results via the central processing apparatus, and sorts the plurality of inspection results into groups in accordance with a predetermined importance order of classified movements, and renders the display part to sequentially display the plurality of inspection results in accordance with the groups.

Since the display device causes the display part to sequentially display the inspection results in accordance with the importance order thereof, and thus this configuration makes it possible to refer to the inspection result in accordance therewith.

A display method according to another aspect is a display method for use in a subject observation system including a sensor unit for inspecting and notifying a predetermined movement of a subject to be observed, a display device for displaying predetermined information, and a central processing apparatus communicatively connected with the sensor unit and the display device respectively to receive from the sensor unit a transmission of an inspection result about an inspection performed by the sensor unit and transmit the inspection result to the display device, the display method including: a communication step of performing a communication; a display step of performing a display on a display part; an input step of receiving a change instruction input for changing a display content being displayed on the display part; a display processing step of displaying the inspection result transmitted from the central processing apparatus on the display part, displaying a code representing a presence of a new inspection result on the display part upon receipt of the transmission of the new inspection result via the communicator, while maintaining the existing display content being displayed on the display part, and displaying the new inspection result on the display part when the input part receives the change instruction input.

In the display method, when the sensor unit inspects a predetermined movement of a subject, a transmission of a new inspection result from the sensor unit is received via the central processing apparatus. In this case, in the display processing step, the code representing a presence of the received new inspection result is displayed on the display part, while the existing display content displayed on the display part is maintained, and further the received new inspection result is displayed on the display part when the input part receives the change instruction input. In this way, the exiting display content is displayed on the display part preferentially to the received new inspection result. Thus, the display method makes it possible to ensure encouragement of an action (execution, reply) to a patient or the like in connection with a previous notification. Moreover, since the code representing the presence of the received new inspection result is further displayed on the display part while the display of the existing display content is maintained, a user such as an observer can, for example, recognize the presence of the received new inspection result.

In a display device according to a further aspect, a sensor unit for inspecting and notifying a predetermined movement of a subject to be observed; any one of the display devices described above for displaying predetermined information; and a central processing apparatus communicatively connected with the sensor unit and the display device respectively to receive from the sensor unit a transmission of an inspection result about an inspection performed by the sensor unit and transmit the inspection result to the display device.

The subject observation system including the display device described above can ensure encouragement of an action (execution, reply) to a patient or the like in connection with a previous notification.

This application is based on Japanese patent application No. 2015-158154 field in Japan Patent Office on Aug. 10, 2015, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

INDUSTRIAL APPLICABILITY

The present invention can provide a display device and a display method for use in a subject observation system, and a subject observation system.

The invention claimed is:

1. A display device among a plurality of display devices each connected to a network for use in a system and operable to receive a notification about a condition of a subject to be observed, the display device comprising:
   a display;
   a communicator which receives the notification about the condition of the subject;
   a hardware processor which renders the display to display information of the subject based on the notification about the condition of the subject received by the communicator; and
   an input which receives an input of an action intention to the subject on the basis of the information of the subject displayed on the display, wherein
   the communicator is structured to perform:
      sending a first signal indicating acceptance of the input of the action intension by the display device to another display device among the plurality of display devices via the network when the input receives the input of the action intention; and
      receiving a second signal indicating acceptance of another input of another action intention to the subject by the another display device to the display device via the network when the another input of the another action intention is accepted by the another display device, and
   the hardware processor further renders the display to display a remaining number of pieces of the information of the subject for which no input of an action intention is accepted by any one of the plurality of display devices.

2. A display device according to claim 1, wherein the hardware processor displays information of a plurality of subjects to be observed by way of scrolling in accordance with an operation of a user to the display on receipt of notifications about respective conditions of the plurality of subjects.

3. A display device according to claim 2, wherein the hardware processor further renders the display to display the information of the plurality of subjects in a chronological order on the basis of a receipt time of each of the notifications corresponding to the information in the communicator.

4. A non-transitory computer-readable recording medium which stores a program to be executed by a computer in a display device including a display among a plurality of display devices each connected to a network for use in a system and operable to receive a notification about a condition of a subject to be observed, the program causing the computer to execute:
   receiving the notification about the condition of the subject;
   displaying on the display information of the subject based on the notification about the condition of the subject received in the receiving step;
   a step of receiving an input of an action intention to the subject on the basis of the information of the subject displayed on the display;
   sending a first signal indicating acceptance of the input of the action intention by the display device to another display device among the plurality of display devices via the network when the input of the action intention is received in the input receiving step;
   receiving a second signal indicating acceptance of another input of another action intention by the another display device to the display device via the network when the another input of the another action intention is accepted by the another display device, wherein
   in the displaying step, a remaining number of pieces of the information of the subject for which no input of an action intention is accepted by any one of the plurality of display devices is further displayed on the display.

5. A non-transitory computer-readable recording medium according to claim 4, wherein the program further causes the computer to execute:
   a step of displaying information of a plurality of subjects to be observed by way of scrolling in accordance with an operation of a user to the display on receipt of notifications about respective conditions of the plurality of subjects.

6. A non-transitory computer-readable recording medium according to claim 5, wherein
   in the displaying step by way of the scrolling, the information of the plurality of subjects is displayed on the display in a chronological on the basis of a receipt time of each of the notifications corresponding to the information in the notification receiving step.

7. A display method to be performed by a display device including a display among a plurality of display devices each connected to a network for use in a system and operable to receive a notification about a condition of a subject to be observed, the display method comprising:
   receiving the notification about the condition of the subject;
   displaying on the display information of the subject based on the notification about the condition of the subject received in the receiving step;
   receiving an input of an action intention to the subject on the basis of the information of the subject displayed on the display;
   sending a first signal indicating acceptance of the action intention by the display device to another display device among the plurality of display devices via the network when the input of the action intention is received in the input receiving step;
   receiving a second signal indicating acceptance of another input of another action intention by the another display device to the display device via the network when the another input of the another action intention is accepted by the another display device, wherein
   in the displaying step, a remaining number of pieces of the information of the subject for which no input of an action intention is accepted by any one of the plurality of display devices is further displayed on the display.

8. A display method according to claim 7, further comprising:
   a step of displaying information of a plurality of subjects to be observed by way of scrolling in accordance with an operation of a user to the display on receipt of notifications about respective conditions of the plurality of subjects.

9. A display method according to claim 8, wherein
   in the displaying step by way of the scrolling, the information of the plurality of subjects is displayed on the display in a chronological on the basis of a receipt time of each of the notifications corresponding to the information in the notification receiving step.

* * * * *